(12) United States Patent
Braun et al.

(10) Patent No.: US 10,377,879 B2
(45) Date of Patent: Aug. 13, 2019

(54) CHEMICAL AMPLIFICATION IN SELF-STRENGTHENING MATERIALS

(71) Applicant: The Board of Trustees of the University of Illinois, Urbana, IL (US)

(72) Inventors: Paul V. Braun, Champaign, IL (US); Shuqi Lai, Urbana, IL (US); Ariane Vartanian, Brooklyn, NY (US)

(73) Assignee: The Board of Trustees of the University of Illinois, Urbana, IL (US)

(*) Notice: Subject to any disclaimer, the term of this patent is extended or adjusted under 35 U.S.C. 154(b) by 1 day.

(21) Appl. No.: 15/786,762

(22) Filed: Oct. 18, 2017

(65) Prior Publication Data

US 2018/0105678 A1  Apr. 19, 2018

Related U.S. Application Data

(60) Provisional application No. 62/409,996, filed on Oct. 19, 2016.

(51) Int. Cl.
| | |
|---|---|
| *C08K 5/42* | (2006.01) |
| *C08K 5/205* | (2006.01) |
| *G01N 21/31* | (2006.01) |
| *C07C 53/18* | (2006.01) |
| *G01R 33/46* | (2006.01) |
| *C08K 5/03* | (2006.01) |

(52) U.S. Cl.
CPC ............... *C08K 5/42* (2013.01); *C08K 5/205* (2013.01); *C07C 53/18* (2013.01); *C08K 5/03* (2013.01); *G01N 2021/3155* (2013.01); *G01R 33/46* (2013.01)

(58) Field of Classification Search
CPC ............. C08K 5/42; C08K 5/205; C08K 5/03
See application file for complete search history.

(56) References Cited

U.S. PATENT DOCUMENTS

| 7,566,747 B2 | 7/2009 | Moore et al. |
| 2006/0252852 A1 | 11/2006 | Braun et al. |
| 2014/0087309 A1 | 3/2014 | Cardineau et al. |

FOREIGN PATENT DOCUMENTS

KR  20050019557 A  * 3/2005

OTHER PUBLICATIONS

Machine translation of KR-20050019557-A. (Year: 2005).*
He et al., "Domino Free Radical Photopolymerization Based on Phototriggered Base Proliferation Reaction and Redox Initiation," J. Polymer Sci., 52(11):1560-1569, Jun. 2014.
He et al., "Phototriggered Base Proliferation: A Highly Efficient Domino Reaction for Creating Functionally Photo-Screened Materials," Macromolecules, 46(16):6402-6407, Aug. 2013.
Kruger et al., "Catalytic and Autocatalytic Mechanisms of Acid Amplifiers for Use in EUV Photoresists," Chem. Mater., 22(19):5609-5616, Sep. 2010.
Mohapatra et al., "Design of Small Molecule Reagents that Enable Signal Amplification via an Autocatalytic, Base-mediated Cascade Elimination Reaction," Chem Commun (Camb)., 48(24):3018-3020, Mar. 2012.

* cited by examiner

*Primary Examiner* — Wenwen Cai
(74) *Attorney, Agent, or Firm* — Haukaas Fortius PLLC; Michael H. Haukaas

(57) ABSTRACT

A self-strengthening material is provided, the material comprising a polymer matrix having a plurality of chemical amplifiers dispersed throughout the polymer matrix and a plurality of triggerable reservoirs, the triggerable reservoirs capable of releasing at least one activator of the plurality of chemical amplifiers, wherein the plurality of chemical amplifiers reacts with the at least one activator to produce additional activators capable of changing the mechanical properties of the polymer matrix, and thus strengthening the material.

20 Claims, 16 Drawing Sheets

Vinyl-1,2-polybutadiene

CHEMICAL AMPLIFICATION IN SELF-STRENGTHENING MATERIALS

RELATED APPLICATIONS

This application claims priority under 35 U.S.C. § 119(e) to U.S. Provisional Patent Application No. 62/409,996, filed Oct. 19, 2016, which is incorporated herein by reference.

BACKGROUND OF THE INVENTION

Cracks and other defects that form within a polymer can be difficult to detect and almost impossible to repair. A successful method of autonomically repairing cracks and other defects that has the potential for significantly increasing the longevity of materials has been described, for example, in U.S. Pat. No. 6,518,330. This self-healing system includes a material containing, for example, solid particles of Grubbs catalyst and capsules containing liquid dicyclopentadiene (DCPD) embedded in an epoxy matrix. When a crack propagates through the material, it ruptures the microcapsules and releases DCPD into the crack plane. The DCPD then mixes with the Grubbs catalyst, undergoes Ring Opening Metathesis Polymerization (ROMP), and cures to provide structural continuity where the crack had been.

Crack formation in coatings can be especially problematic, since coatings are often present to protect the substrate onto which they have been coated. For example, metal substrates may be coated with a layer of material to prevent or inhibit corrosion of the metal. A crack in such a coating typically leads to corrosion of the underlying metal, resulting in expensive and wasteful repair or replacement of some or all of a part made from the metal. To ensure the integrity of the metal, it may be necessary to replace the coating periodically, regardless of whether cracks actually have formed. Coatings also may be used in the form of primers, paints, stains, sealers and topcoats. Substrates for these coatings include building materials, windows, electronics, automotive parts, marine parts and aerospace parts. These coatings may protect the underlying material from corrosion, moisture, bacterial growth, ultraviolet radiation and/or mechanical impact.

Extrinsic self-healing is a straightforward approach to healing damaged materials and elongating material lifetime. This is a type of process that is initiated by healing agents released from micro- or nano-scale containers that were embedded in a substrate. However, this process can require long healing times and high healing temperatures due to limited loading of healing agents, slow delivery of healing agents to the damage sites, and slow reaction kinetics. At an early stage of a damage event, such as when cracks are microscopic in size, or even before observable damage occurs, self-strengthening, a specific subgroup of self-healing, can be used as a preventive strategy to increase material strength and prevent further material damage. A significant portion of self-strengthening materials are stimuli responsive and able to convert otherwise neutral or destructive environmental triggers (e.g., mechanical force, light, acids, bases, etc.) to constructive processes.

It is desirable to provide a self-strengthening, and even more broadly self-healing systems in which minor triggers (such as bond scission, the rupture of only a few microcapsules, or the activation of a mechanophore) can result in strengthening of a material at a lower temperature and at a faster rate, and so materials which can take a minor event, and turn it into a significant response are highly desirable.

SUMMARY

Autocatalytic reactions are one special category of stimuli-responsive reactions, at least one of whose products can act as the stimulus to trigger its own formation. Notably, autocatalytic reactions are advantageous over other stimuli-responsive reactions due to their low energy input requirements and ability to self-sustain the process. Considering that acids and bases are ubiquitous and widely used in various chemical reactions, this disclosure focuses on acid and base amplification reactions, which proceed autocatalytically in the presence of acids and bases, respectively. To improve otherwise sluggish low temperature extrinsic self-healing or self-strengthening, this disclosure utilizes acid amplifiers and base amplifiers to amplify the amount of acidic or basic strengthening agents and accelerate mass transport of strengthening agents in solids. When damage occurs and results in the release of a small amount of acidic or alkaline strengthening agents from mechanophores or such reservoirs of strengthening agents like capsules and core-shell fibers, corresponding amplification reactions will be initiated to increase the amount of strengthening agents that can be delivered to the damage sites as well as accelerating mass transport of strengthening agents in solid materials. Thus, more efficient material recovery at lower temperature is achieved compared to conventional extrinsic self-healing or self-strengthening materials.

Accordingly, this disclosure provides a self-reinforcing material comprising: (a) a polymer doped with a chemical amplifier, wherein the chemical amplifier is capable of amplifying a change in pH at a locus within the polymer; and (b) a plurality of triggerable reservoirs comprising an activator, wherein a triggerable reservoir is capable of releasing a catalytic quantity of an activator that induces the autocatalytic decomposition of the chemical amplifier in response to a mechanical stimulus at the locus;

wherein when the chemical amplifier amplifies a change in local pH at the locus of the mechanical stimulus, it reacts with the catalytic quantity of the activator released by the triggerable reservoir in response to the mechanical stimulus, thereby changing the chemical and physical properties of the polymer.

Additionally, this disclosure provides a method to prepare a self-reinforcing material, the method comprising: coating a substrate with a polymer layer doped with a stabilized acid or base amplifier, metal salts, and a plurality of triggerable reservoirs (e.g., microcapsules, core-shell fibers, mechanophores, etc.) comprising an acid or base catalyst, wherein the acid or base amplifier is capable of amplifying a change in pH at a locus within the polymer layer, and wherein a triggerable reservoir is capable of releasing a catalytic quantity of an acid catalyst or a base catalyst that induces the autocatalytic decomposition of the acid or base amplifier in response to a mechanical stimulus at the locus;

wherein when a mechanical stimulus causes damage to the coated substrate, the acid or base amplifier amplifies a change in local pH at the locus of the mechanical stimulus when it reacts with the catalytic quantity of the acid catalyst or the base catalyst released by the triggerable reservoir in response to the mechanical stimulus, thereby forming a cross-linked metallopolymer to form a self-reinforced material at the locus of the mechanical stimulus.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
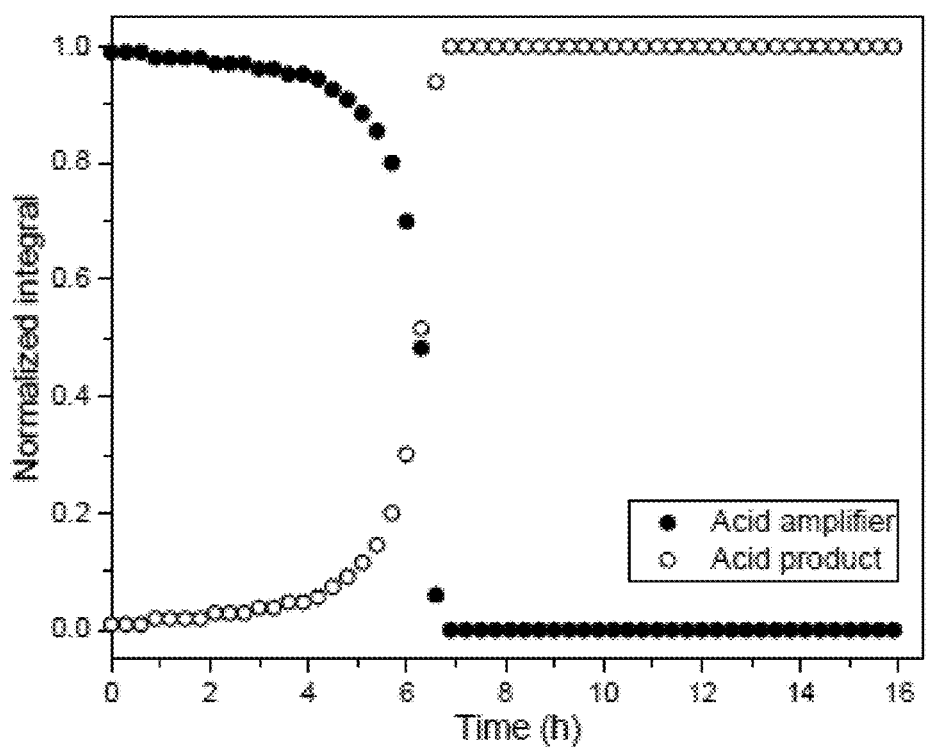
FIG. 1. A graph of the conversion of an acid amplifier to its acid product in the presence of an acid activator over time.

Triggerable cross-linking is a straightforward approach to strengthening materials and elongating material lifetime, but can require continuous trigger exposure, long reaction times and high temperatures due to limited loading of reactive agents, slow delivery of reactive agents to the damage sites, and slow reaction kinetics. The present disclosure improves self-strengthening via incorporation of chemical amplifiers. Specifically, the improvement is achieved through solving problems faced by conventional self-strengthening materials: (i) triggered by the activators released in a damage event, chemical amplifiers start to decompose to generate additional activator (which is also capable of changing the mechanical properties of the polymer matrix, e.g. cross-linking) to both participate in strengthening reactions and drive the decomposition of additional chemical amplifiers; and (ii) by coupling reaction and diffusion of the activator, higher mass transport rate can be expected compared to that usually observed in Fickian diffusion of molecules in solids. Increased concentration of agent participating in the strengthening reactions, and increased transport rates result in a self-strengthening material with shorter strengthening time, and a self-strengthening material that does not necessarily require a continuous trigger exposure for substantial strengthening to take place.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "triggerable reservoir" as used herein, can be a micro, nano or molecular storage device for a chemical wherein the chemical is released when the chemical storage device is ruptured due to some external force causing (or triggering) it to rupture. For example, microcapsules can house a substance within its shell, and the substance is released to the microcapsule's immediate environment when the shell opens. As another example, there are molecules which release acid when subjected to a mechanical stress.

The term "microcapsule" refers to a hollow spherical structure with a liquid core. Core-shell fibers can be considered as a high-aspect-ratio counterpart of microcapsules.

Embodiments of the Invention

This disclosure provides a self-reinforcing material comprising:

(a) a polymer doped with a chemical amplifier, wherein the chemical amplifier is capable of amplifying a change in pH at a locus within the polymer; and (b) a plurality of triggerable reservoirs comprising an activator, wherein a triggerable reservoir is capable of releasing a catalytic quantity of an activator that induces the autocatalytic decomposition of the chemical amplifier in response to a mechanical stimulus at the locus;

wherein when the chemical amplifier amplifies a change in local pH at the locus of the mechanical stimulus, it reacts with the catalytic quantity of the activator released by the triggerable reservoir in response to the mechanical stimulus, thereby changing the chemical and physical properties of the polymer.

In various embodiments of the self-reinforcing material, the polymer comprises a polysiloxane, a poly[poly(ethylene glycol) acrylate], a polybutadiene, an epoxy, a catechol-containing polymer, or a combination thereof. In additional embodiments, the polymer comprises polydimethylsiloxane, poly[poly(ethylene glycol) methyl ether acrylate-dopamine acrylamide] (PPD), poly[di(ethylene glycol) methyl ether methacrylate-dopamine acrylamide](PDD), vinyl-polybutadiene, cis-polybutadiene, a phenolic epoxy, or a combination thereof. In yet other various embodiments, the polymer may be a bulk polymer or a polymer coating.

In additional embodiments, the triggerable reservoir is a microcapsule, a core-shell fiber, a mechanophore, or a combination thereof. In other embodiments, the triggerable reservoir comprises the activator, wherein the activator is an acid catalyst or a base catalyst. In yet other various embodiments, the chemical amplifier is an acid amplifier or a base amplifier.

In various additional embodiments, the ratio of the acid or base amplifier to the acid or base catalyst ranges from about 5:1 to about 500:1, and wherein the acid catalyst can include but is not limited to trifluoroacetic acid or the base catalyst can include but is not limited to 4-benzylpiperidine. Other additional embodiments of the said ratio range from about 5:1 to about 250:1, about 10:1 to about 100:1, or about 20:1 to about 100:1.

In other various embodiments, the structure of the base amplifier is:

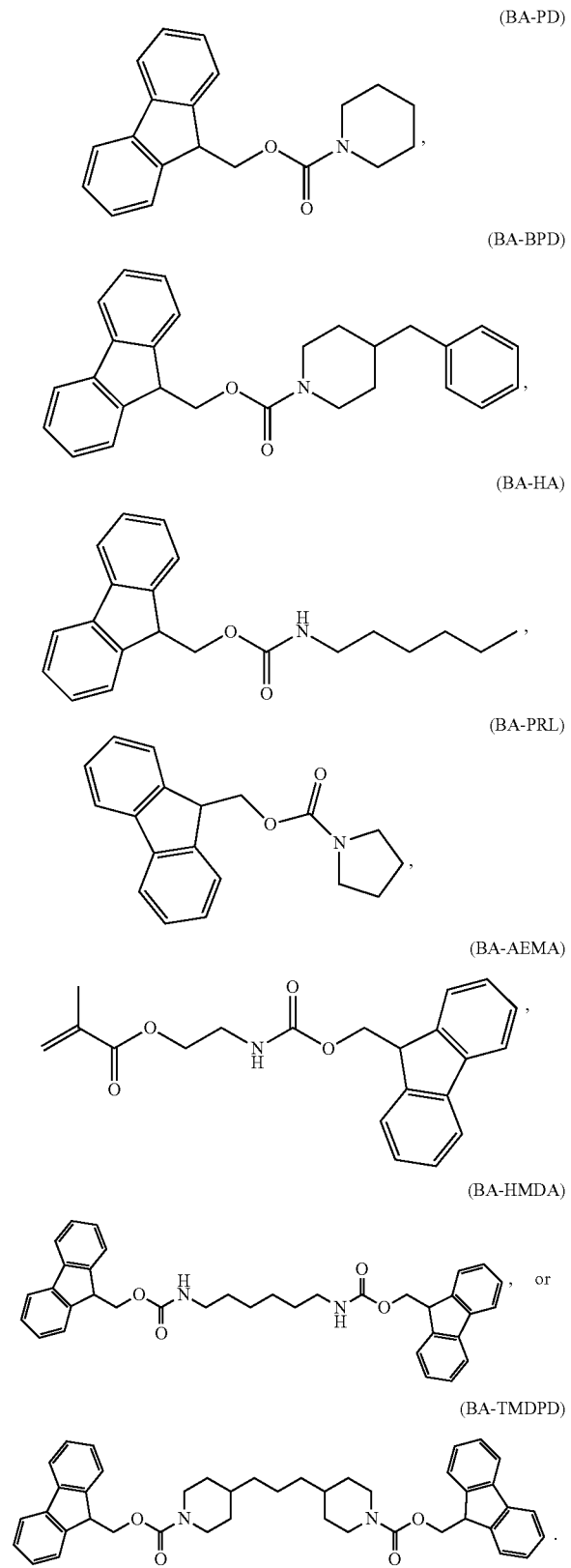

In yet other additional embodiments, the structure of the acid amplifier is:

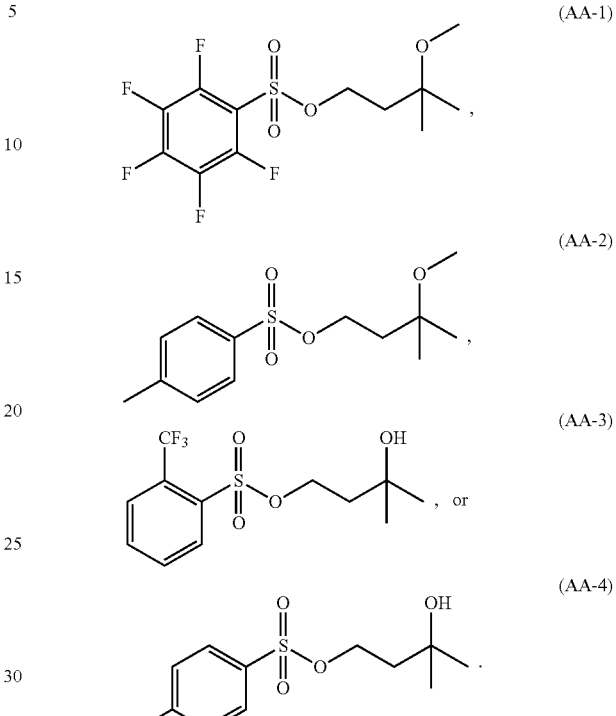

In various embodiments, the base amplifier releases a second base upon contact with the base catalyst to autocatalytically release additional second base as the base amplifier decomposes. In yet other embodiments, the acid amplifier releases a second acid upon contact with the acid catalyst to autocatalytically release additional second acid as the acid amplifier decomposes.

In additional embodiments, the polymer is cross-linked at the locus of the mechanical stimulus, thermal stimulus, chemical stimulus or irradiative stimulus. In other embodiments the polymer can comprise one or more different polymers capable of being cross-linked.

In a variety of additional embodiments, the polymer is doped with a metal salt. In yet other embodiments, the metal salt is a salt of iron, nickel, copper, zinc, magnesium, chromium, cobalt, tin, lead, aluminum, calcium, or a combination thereof. In some embodiments, the polymer is a metallopolymer at the locus of the mechanical stimulus.

In other embodiments, the chemical amplifier is stabilized. In yet other embodiments, the chemical amplifier is stabilized by the addition of either an acid or a base. In various embodiments, the base amplifier is stabilized by an acid. In additional embodiments, the base amplifier is stabilized by trifluoroacetic acid, acetic acid, hydrochloric acid, sulfuric acid, an organic acid, or a mineral acid. In other additional embodiments, the acid amplifier is stabilized by a non-nucleophilic base. In yet more embodiments, the acid amplifier is stabilized by a base, wherein the base is an organic amine, sodium hydroxide, or an inorganic base.

In yet other additional embodiments, the locus of an amplified change in pH is at the position of a triggerable reservoir, wherein the triggerable reservoir was triggered to release a catalytic quantity of an activator by a mechanical stimulus at or near the locus. In various other embodiments, the locus has a radius of about 0.1 nm to about 5 mm from a triggered, triggerable reservoir. The radius can also range from about 1 nm to about 1 mm, about 10 nm to about 0.5 mm, about 100 nm to about 0.1 mm, about 1 μm to about 100 μm, about 10 μm to about 1 mm, or about 100 μm to about 2 mm.

This disclosure also provides a method to prepare a self-reinforcing material, the method comprising:

coating a substrate with a polymer layer doped with a stabilized acid or base amplifier, metal salts, and a plurality of triggerable reservoirs comprising an acid or base catalyst, wherein the acid or base amplifier is capable of amplifying a change in pH at a locus within the polymer layer, and wherein a triggerable reservoir is capable of releasing a catalytic quantity of an acid catalyst or a base catalyst that induces the autocatalytic decomposition of the acid or base amplifier in response to a mechanical stimulus at the locus;

wherein when a mechanical stimulus causes damage to the coated substrate, the acid or base amplifier amplifies a change in local pH at the locus of the mechanical stimulus when it reacts with the catalytic quantity of the acid catalyst or the base catalyst released by the triggerable reservoir in response to the mechanical stimulus, thereby forming a cross-linked metallopolymer to form a self-reinforced material at the locus of the mechanical stimulus.

In other embodiments of the above disclosure, the polymer is not doped with metal salts. In yet other embodiments of the above disclosure, the self-reinforced material formed is from cross-linking of an organic polymer. In additional embodiments of the above disclosure, a mechanical stimulus can instead be a thermal stimulus, an irradiation stimulus, or a chemical stimulus.

In various embodiments, the metallopolymer is formed at ambient temperature, or a temperature of about 15° C. to about 35° C. In additional embodiments, the metallopolymer is formed by heating the locus of a mechanical stimulus to a temperature up to about 100° C. In other embodiments the said temperature is up to about 75° C., about 50° C., about 40° C., about 30° C., about 25° C., about 10° C., or about 0° C.

Results and Discussion

The present disclosure provides a self-strengthening composite material comprising a polymer matrix having a chemical amplifier and a plurality of triggerable reservoirs, for example mechanophores or activator reservoirs (e.g. microcapsules, core-shell fibers) dispersed throughout the polymer matrix. These triggerable reservoirs within the polymer matrix are capable of releasing at least one activator of the plurality of chemical amplifiers, wherein the plurality of chemical amplifiers reacts with the at least one activator to produce additional at least one activator, wherein the at least one activator is capable of changing the mechanical properties of the polymer matrix, e.g. is a cross-linking agent capable of inducing cross-linking of the polymer matrix. Following a damage event, one or more triggerable reservoirs release at least one activator into the polymer matrix. The activator reacts with the chemical amplifiers dispersed throughout the polymer to produce additional at least one activator, wherein the activator is capable of inducing mechanical property change to the polymer matrix, for example, it induces self-strengthening by causing the polymer matrix to cross-link in its presence. In addition, the activated chemical amplifier can act as an activator to cause additional production of the activator from other chemical amplifiers embedded in the matrix, producing more mechanical property change to the polymer matrix (e.g.

cross-linking). This results in a greater quantity of available cross-linking agent, and more effective diffusion of the cross-linking agent through the matrix. Notably, these reactions take place at relatively low temperatures. For example, some acid amplification and base amplification reactions can occur at room temperature. Productive chemistries driven by the chemical amplifier other than cross-linking are also possible.

The polymer matrix can be made of one or more polymers. The term polymer includes soluble and/or fusible molecules having long chains of repeat units, and also includes insoluble and infusible networks. The polymer matrix can include one or more polymers including, but not limited to, vinyl-polybutadiene, cis-polybutadiene, epoxy- and catechol-containing polymers, and combinations thereof.

Chemical amplifiers are chemical substances capable of undergoing autocatalytic stimuli-responsive reactions. In one embodiment, the chemical amplifier can be either an acid or a base amplifier, but can also be other chemicals that undergo autocatalytic reactions with at least one product that can act as an activator and is capable of changing the mechanical properties of the polymer matrix. The chemical amplifier can include, but is not limited to an acid amplifier, a base amplifier, a thiol amplifier, a hydrogen peroxide ($H_2O_2$) amplifier, and a fluoride amplifier.

An acid amplifier is a chemical which, in response to the presence of a corresponding activator, produces an acidic product which can act as the stimulus to trigger the formation of more acidic product, and can also act as a cross-linker or a catalyst for cross-linking reactions. Acid amplifiers can include, but are not limited to, the acid amplifiers having the following structures (Scheme 1):

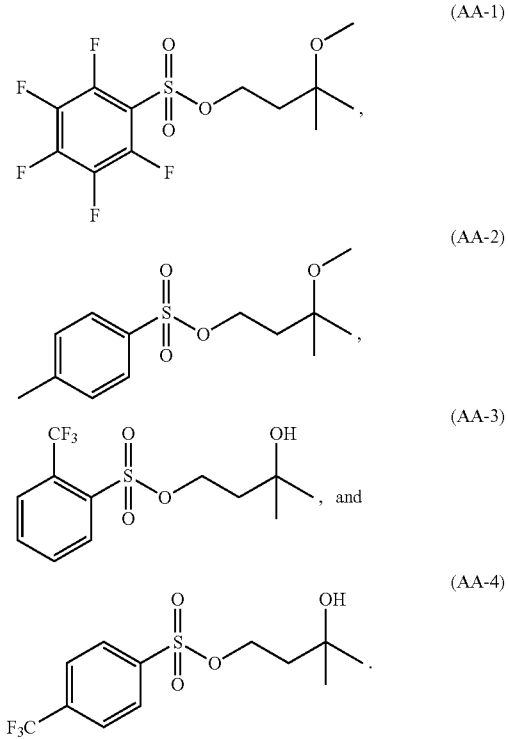

The corresponding activator for an acid amplifier is any chemical that initiates the autocatalytic reaction of the acid amplifier, usually an acid.

A base amplifier is a chemical which, in response to the presence of a corresponding activator, produces a basic product which can act as the stimulus to trigger the formation of more basic product. Base amplifiers can include, but are not limited to, BA-PD, BA-BPD, BA-HA, BA-PRL, BA-AEMA, BA-HMDA, and BA-TMDPD having the following structures (Scheme 2):

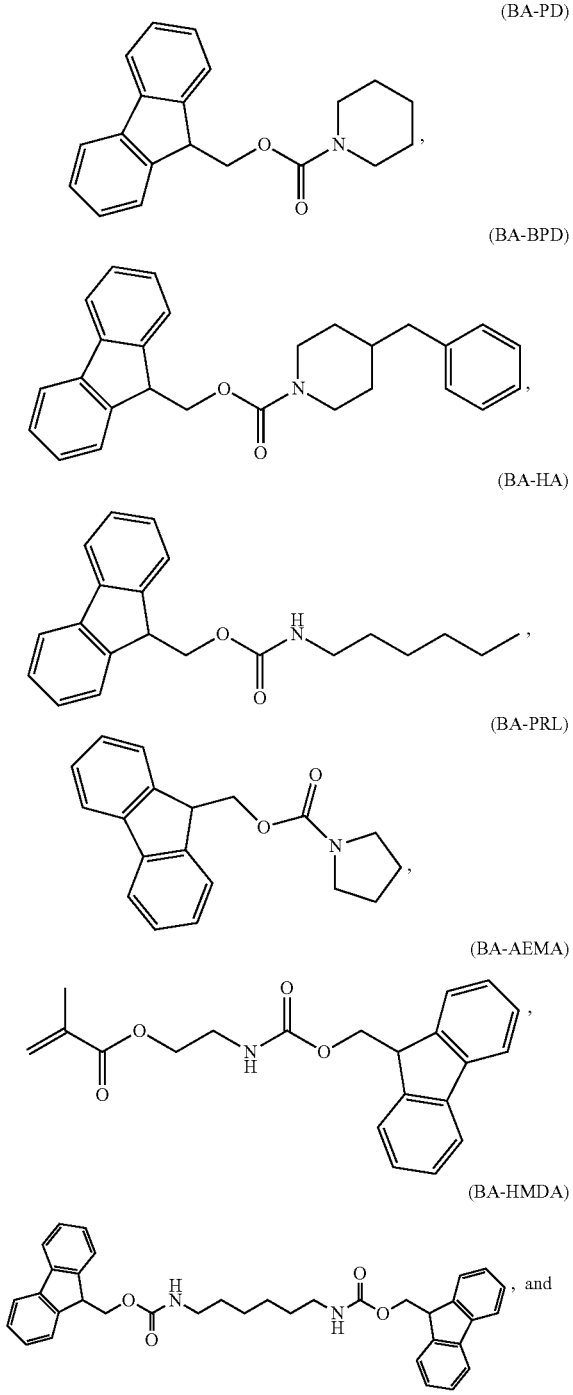

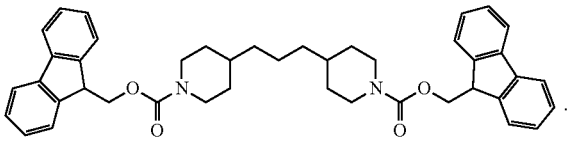

The corresponding activator for a base amplifier is any chemical that initiates the autocatalytic reaction of the base amplifier, usually a base.

An activator can be any chemical that initiates an autocatalytic reaction with the chemical amplifiers. An activator reacts with the chemical amplifier and leads to the production of additional activators. The activator can also be a cross-linking agent. Release of a small amount of activator/cross-linking agent will lead to an autocatalytic reaction leading to more activator/cross-linking agent, and lead to changes in the mechanical properties of the polymer matrix, for example, increased cross-linking of the polymer matrix. In one embodiment, the activator is an acid or a base. The activator can include, but is not limited to, trifluoroacetic acid (TFA), hydrochloric acid (HCl), piperidine, 4-benzylpiperidine, hexylamine, 4,4'-trimethylenedipiperidine, EPI-KURE 3274, and 1,8-diazabicyclo[5.4.0]undec-7-ene (DBU).

A triggerable reservoir can be used to store the activator and release it following a damage event. Reservoirs are hollow closed objects that contain the activator, keeping the activator separate from the matrix until damage occurs. When a damage event occurs, the reservoirs in the affected area rupture and release the contained activator into the matrix to initiate autocatalytic reactions with the chemical amplifiers. The reservoirs can include, but are not limited to, capsules and core-shell fibers.

The triggerable reservoir can also be a mechanophore. A mechanophore is any compound whose reaction is triggered by mechanical force. In the present disclosure a mechanophore is a stress- or strain-activated molecular unit that is inserted into a polymeric material and can respond to mechanical damage. When a damage event occurs, the mechanical force triggers a reaction in the mechanophores, where one product is an activator for the chemical amplifiers embedded in the polymer matrix. For example, a mechanophore capable of releasing acid under mechanical stress was described in *J. Am. Chem. Soc.* 2012, 134, 12446-12449.

The self-strengthening material of the present disclosure can be used as a composite building material or a protective coating for a variety of substrates. Coatings may be used in the form of primers, paints, stains, sealers and topcoats. Substrates for these coatings include building materials, windows, electronics, automotive parts, marine parts, aerospace parts, and any other substrate that is prone to damage which can be curtailed by applying a coating or making out of a self-strengthening composite. These coatings may protect the underlying material from corrosion, moisture, bacterial growth, ultraviolet radiation, mechanical impact and the like.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Conversion of the Acid Amplifier and the Acid Product in the Presence of a Corresponding Activator An acid amplifier, with the chemical structure AA-1 shown in Scheme 1, was reacted with dilute trifluoroacetic acid (TFA, amplifier:activator=100:1, mol:mol), a corresponding activator, in benzene-$d_6$ at 60° C. FIG. 1 shows a graph of the results of this reaction, as quantified by normalized integrals of $^1$H NMR spectroscopy resonances. Within seven hours, virtually all of the acid amplifier had been reacted and converted to its corresponding acid product. Most of the acid amplifier was reacted within about two hours after the initial induction period.

Figure 2:
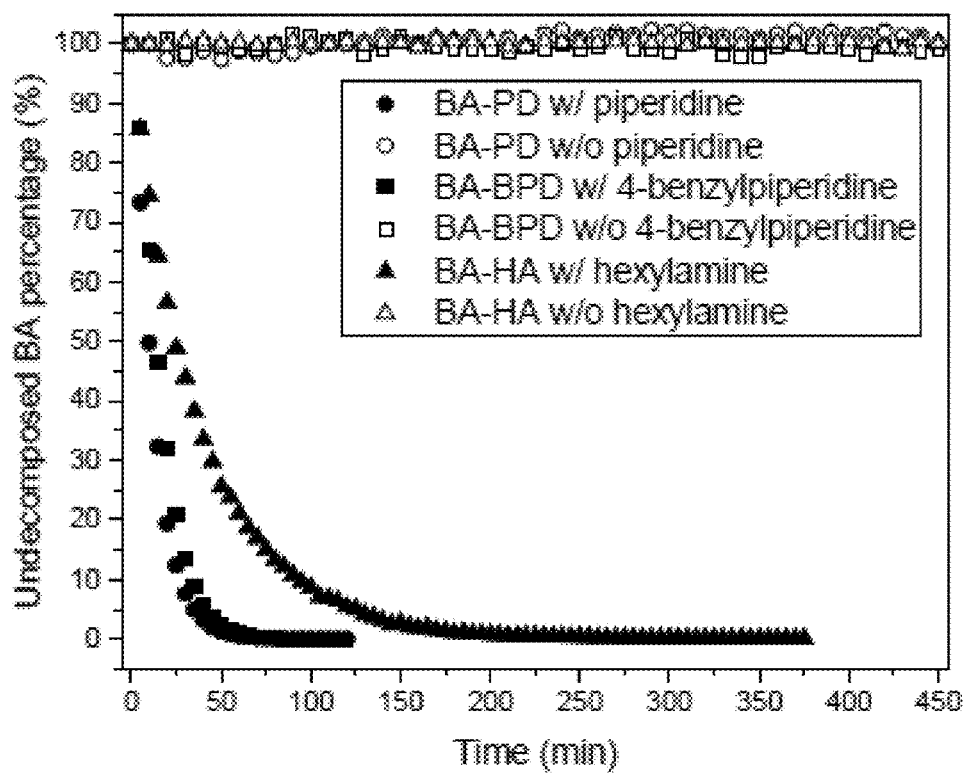
FIG. 2. A graph of the decomposition of 3 different base amplifiers over time with and without a base activator to trigger the reaction.
Figure 3:
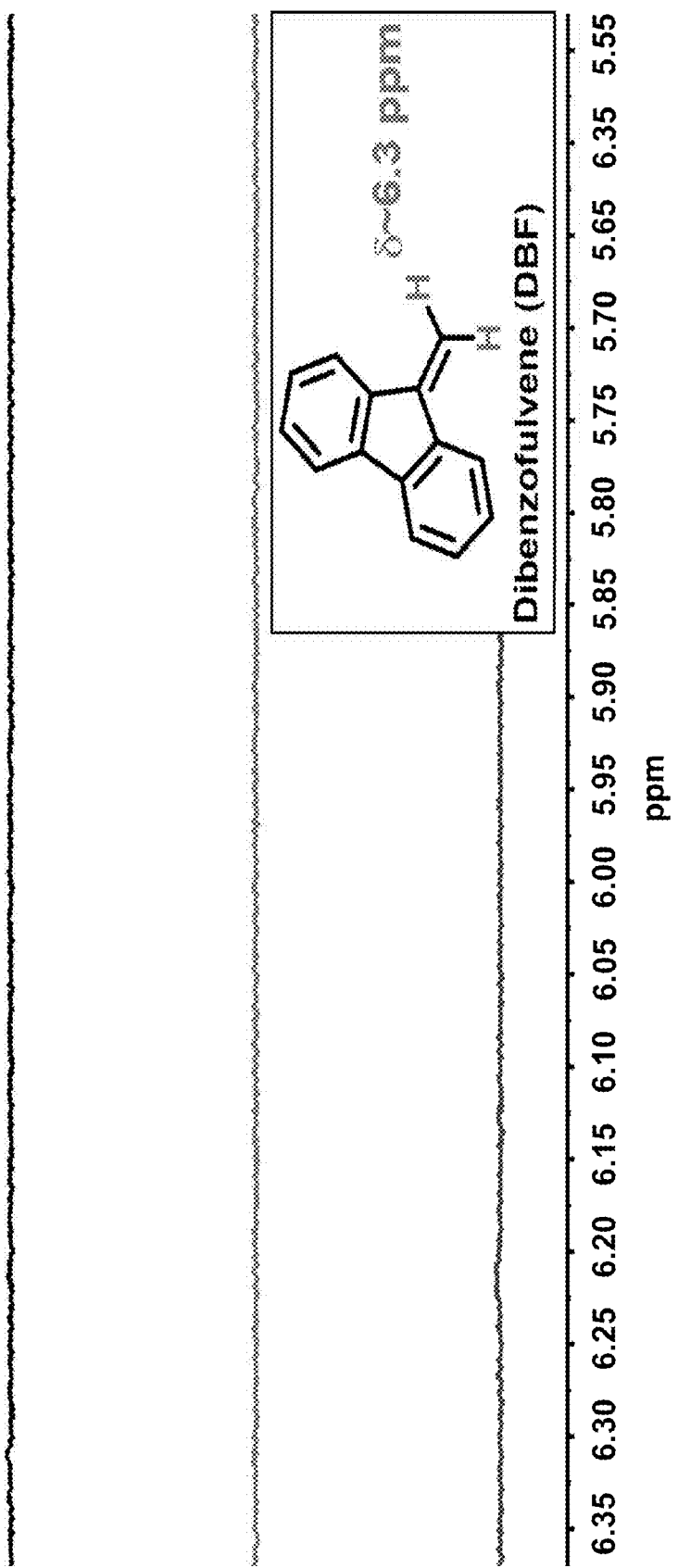
FIG. 3. $^1$H NMR spectra of solutions of base amplifiers in 1 mM TFA/DMSO-$d_6$ after 19 months. No peak of dibenzofulvene, a decomposition product, can be detected.
Figure 4:
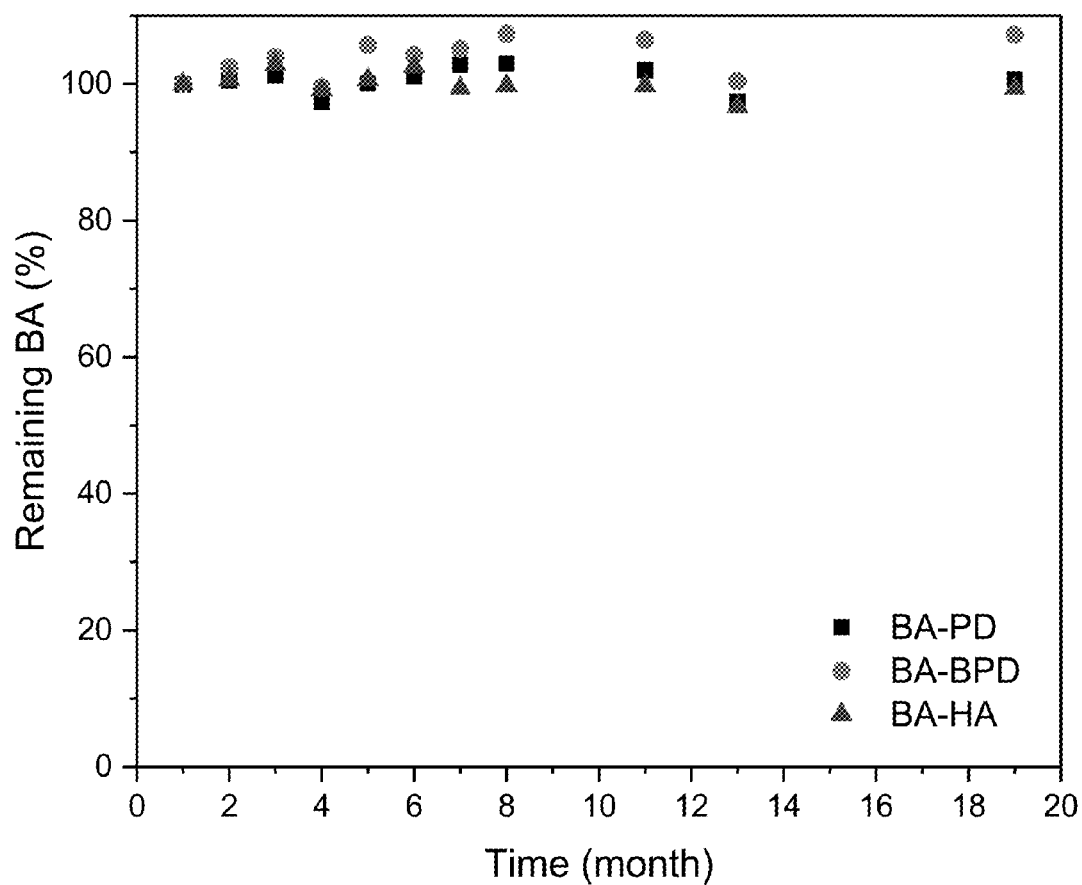
FIG. 4. Stability of base amplifiers over time.

Example 2. Decomposition of Base Amplifiers with and without Corresponding Activators Base amplifiers BA-PD, BA-BPD, and BA-HA, whose chemical structures are shown in Scheme 2, were placed in DMSO-$d_6$ containing 1 mM TFA at 25° C. with and without corresponding activators. The base product for each base amplifier was used as the activator, although theoretically any base can be used to initiate the decomposition. FIG. 2 is a graph of the decomposition of each base amplifier with and without a corresponding activator (amplifier:activator=20:1, mol:mol). Each base amplifier in the presence of its corresponding activator was nearly completely decomposed within 200 minutes of the base amplifier and activator being combined, BA-PD and BA-BPD were nearly completely decomposed within 75 minutes. Absent the corresponding activator, all three base amplifiers remained virtually completely undecomposed after over 1 year. FIG. 3 shows NMR spectra of solutions of base amplifiers in 1 mM TFA/DMSO-$d_6$ after 19 months, and no peak of dibenzofulvene, a decomposition product, can be detected. Thus, base amplifiers stored under ambient conditions for over 1 year (w/o activator), show no peaks of the decomposition product that would show up at ~6.3 ppm. Shown in FIG. 4, integrals of peaks of base amplifiers relative to an internal standard show little decrease in this period, except for some extent of fluctuation due to errors of integration. Tracking the concentration of base amplifiers within 19 months showed no observed decomposition of these amplifiers. Both results indicate that by adding a small amount of trifluoroacetic acid (1 mM) into the solution, background/thermal decomposition (w/o activator) of base amplifiers can be essentially eliminated. This is in sharp contrast to what has been previously reported, where base amplifiers alone decompose quickly in DMSO-$d_6$.

Figure 5:
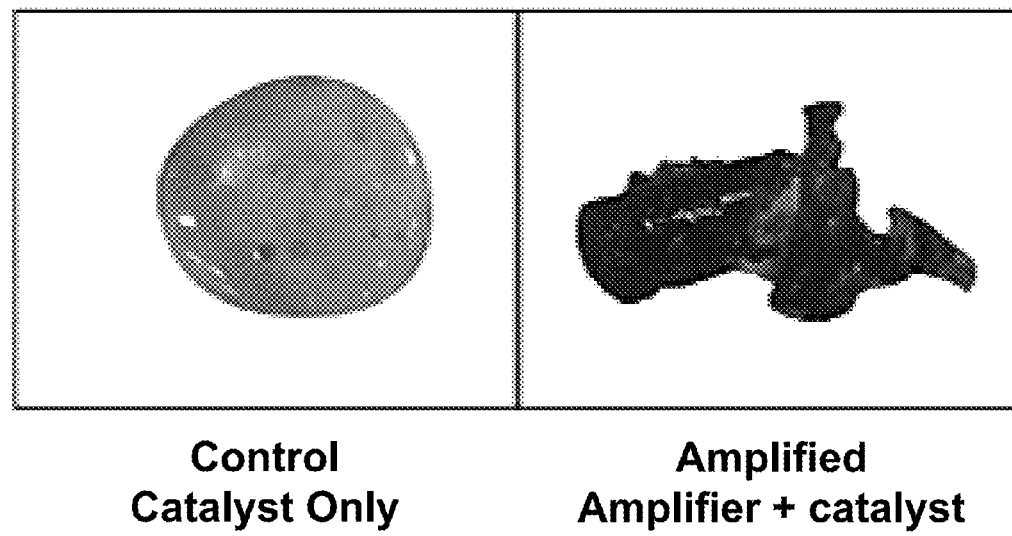
FIG. 5. A pair of optical images comparing vinyl-1,2-polybutadiene with the catalyst trifluoroacetic acid only and vinyl-1,2-polybutadiene with the catalyst trifluoroacetic acid and the acid amplifier, AA-1.

Example 3. Comparison of a Polymer Embedded with Activator Only Vs. a Polymer Embedded with Both Amplifier and Activator Vinyl-1,2-polybutadiene was loaded with the acid activator TFA at 70° C. One sample was also loaded with the acid amplifier AA-1 from Scheme 1. The control sample, containing only TFA, remained a viscous liquid. The sample containing both the acid amplifier and TFA underwent macroscopic changes from a viscous liquid to a solid. FIG. 5 is an optical image of the results of this experiment.

Figure 6:
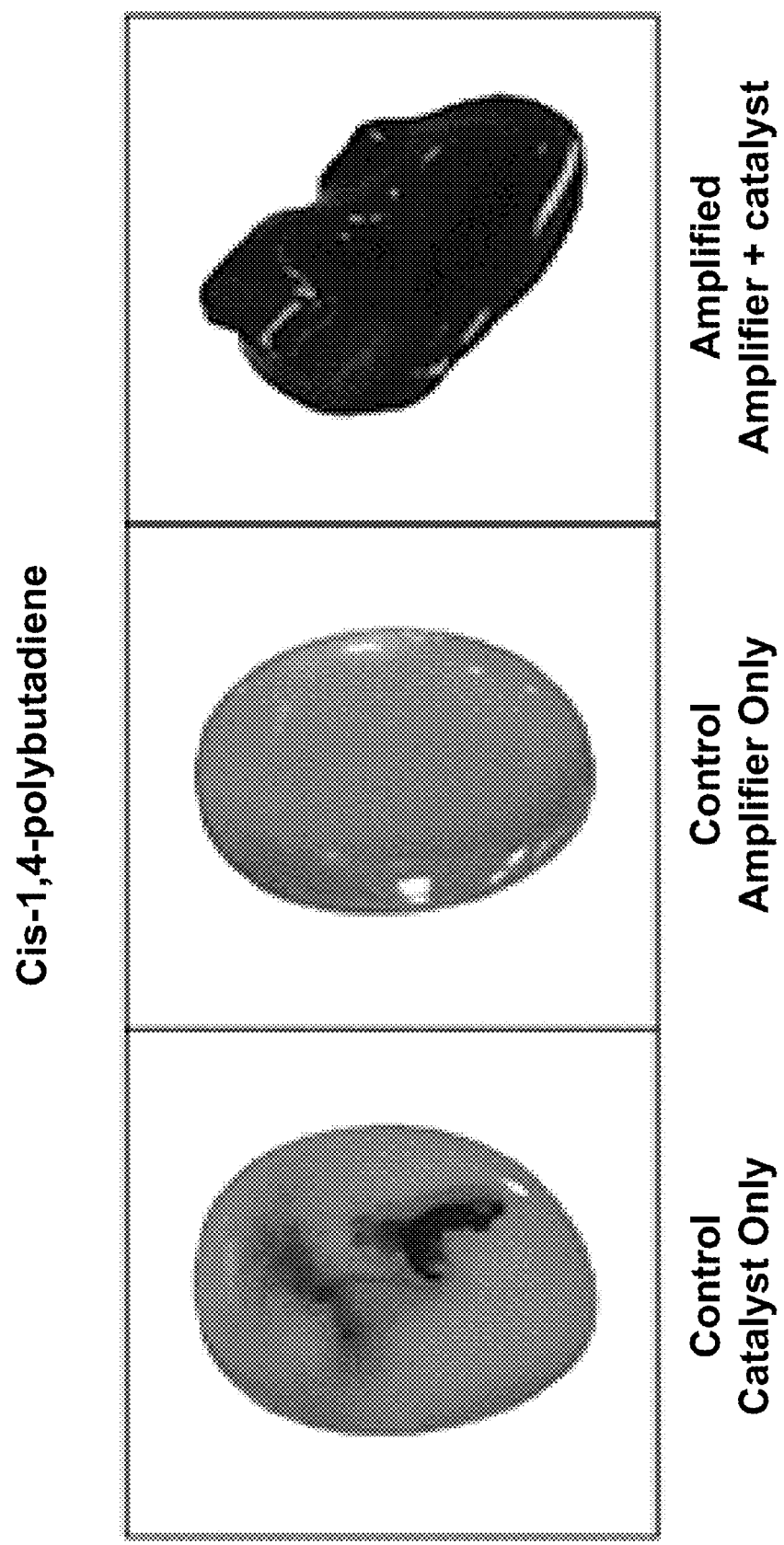
FIG. 6. A series of optical images comparing cis-1,4-polybutadiene with the catalyst trifluroacetic acid only, with the acid amplifier, AA-1 only, and with the acid amplifier and trifluoroacetic acid.

Example 4. Comparison of a Polymer Embedded with Activator Only, Amplifier Only, or Both Amplifier and Activator Three cis-1,4-polybutadiene samples were prepared, one loaded with the activator TFA only, another loaded with the acid amplifier AA-1 from Scheme 1 only, and another loaded with both TFA and the acid amplifier. The sample loaded with only TFA and the sample loaded with only the acid amplifier both remained mostly a viscous liquid. The sample containing both the acid amplifier and TFA underwent global macroscopic changes from a viscous liquid to a solid. FIG. 6 is an optical image of the results of this experiment.

Figure 7:
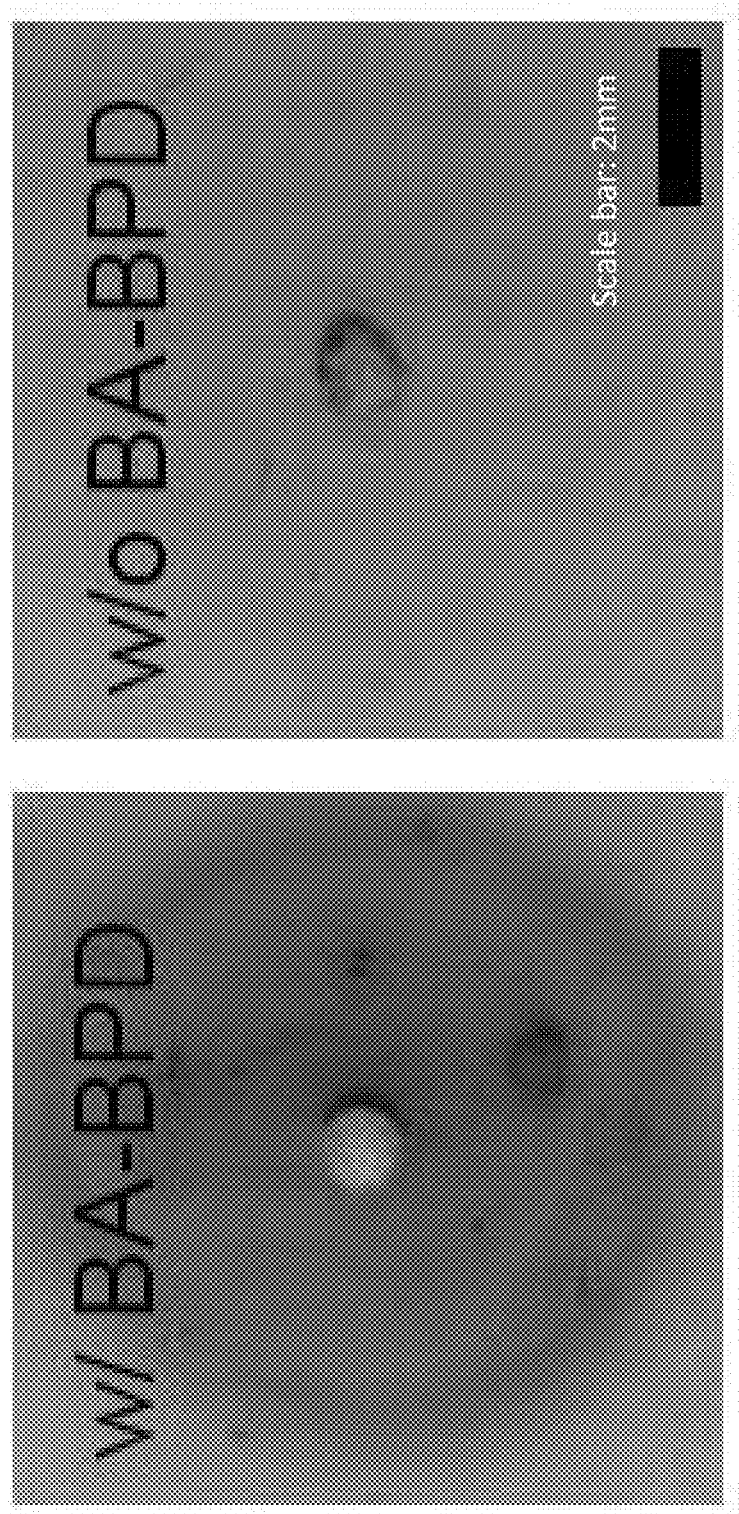
FIG. 7. The optical image on the left displaying the result of the addition of base activator 4-benzylpiperidine to a polydimethylsiloxane (PDMS) matrix containing the base amplifier BA-BPD and a pH indicator (e.g., 2',7'-dichlorofluorescein turns from yellow to red when base accumulates). The optical image on the right displaying the result of the addition of 4-benzylpiperidine to a PDMS matrix containing just a pH indicator.
Figure 8A:
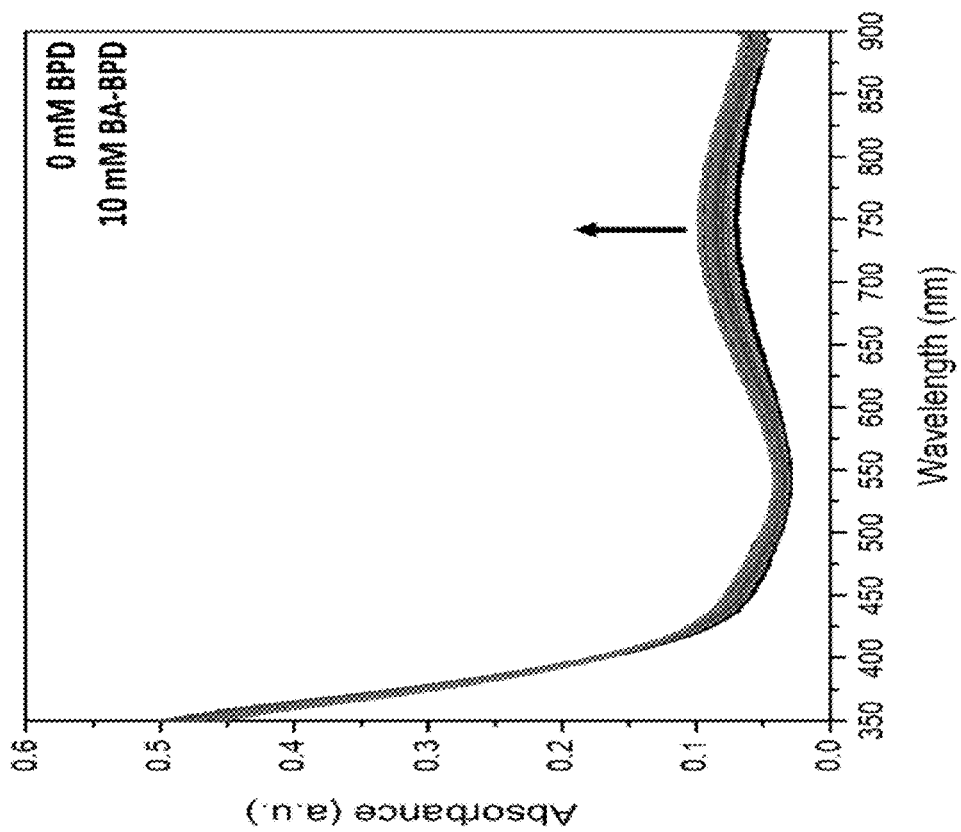
FIG. 8A-8F. Time-lapse UV-Vis spectra for solutions of base amplifier at room temperature within 2 h after addition of different concentrations of base activator (5 min interval).
Figure 8B:
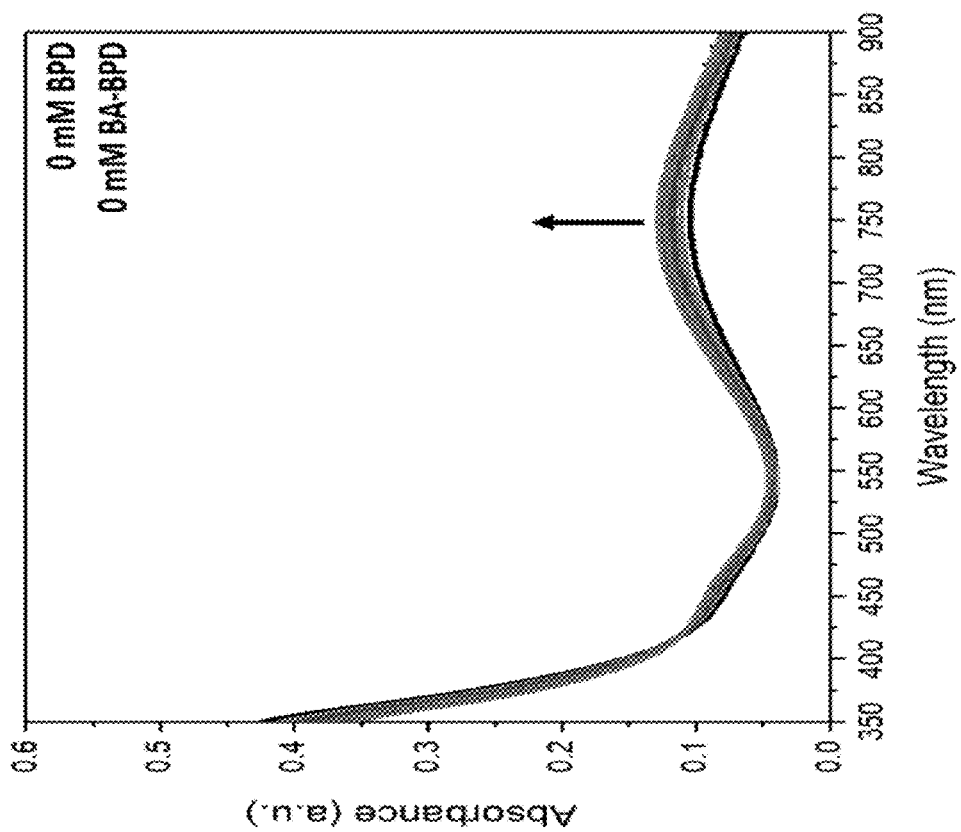
Figure 8C:
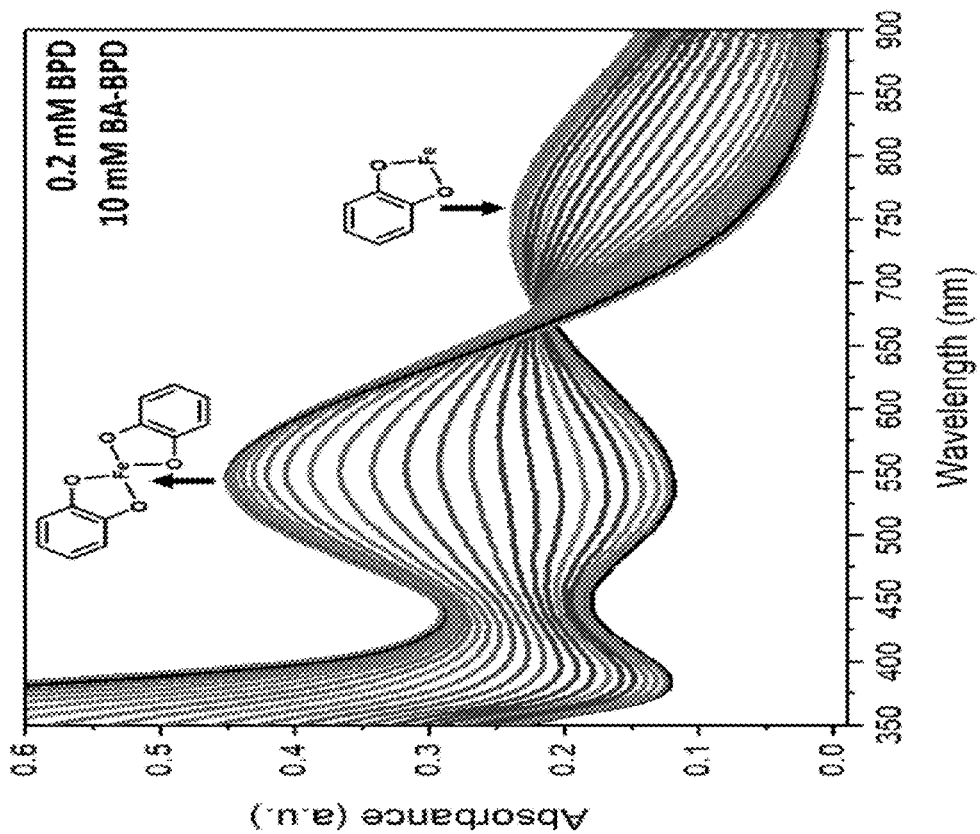
Figure 8D:
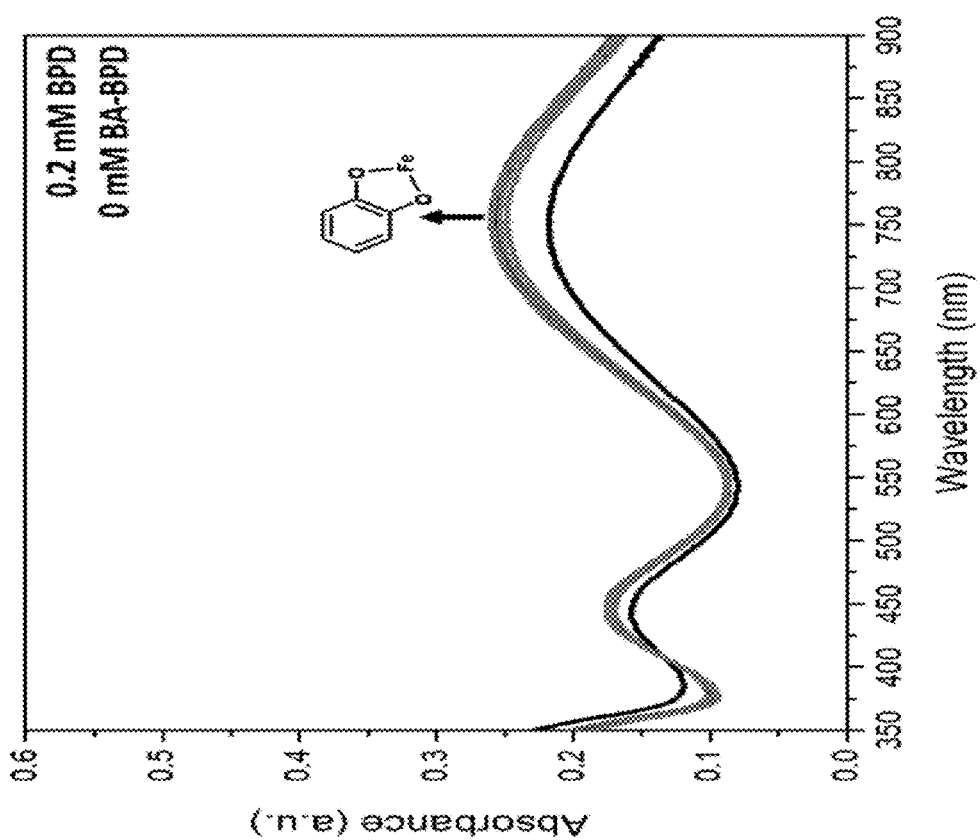
Figure 8E:
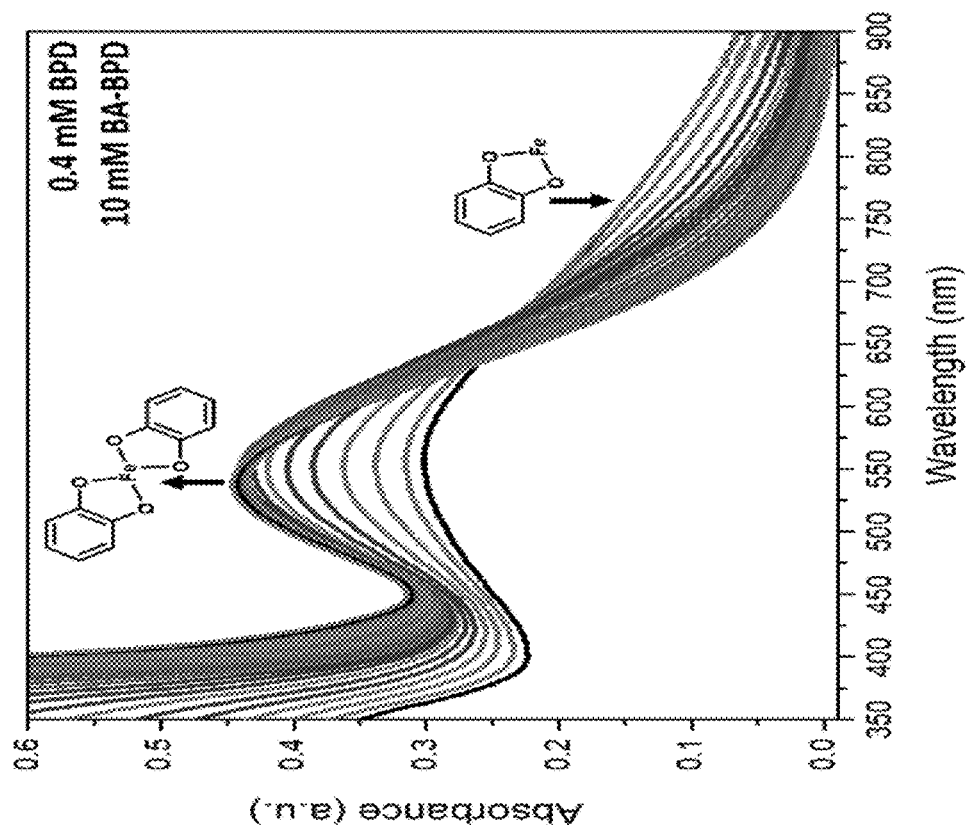
Figure 8F:
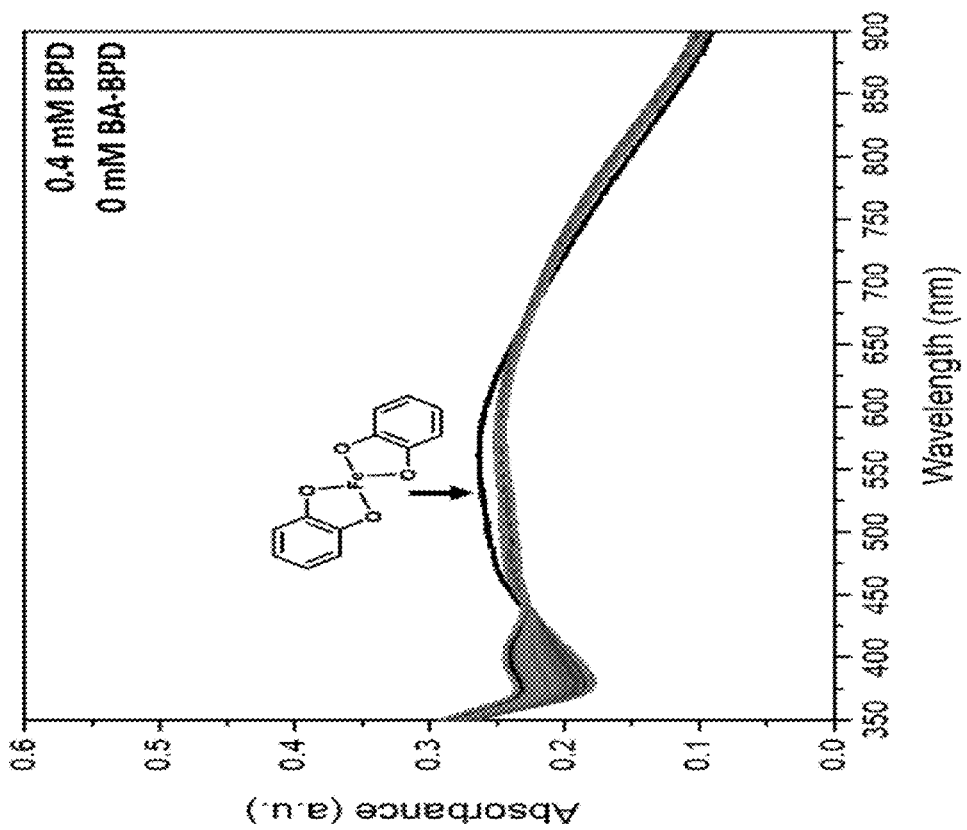

Example 5. Comparison of Diffusion of Base in PDMS Matrixes with and without Embedded Base Amplifier The base activator 4-benzylpiperidine was dropped onto two samples of a PDMS matrix containing 2',7'-dichlorofuorescein, a pH indicator turning from yellow to red when base accumulates. One of the samples was embedded with the base amplifier BA-BPD in Scheme 2, the other was not. For the sample containing the BA-BPD, the pH indicator embedded in the matrix within a radius of a few mm turned from yellow to obviously red. For the sample without the BA-BPD, the pH indicator turned from yellow to obviously red only where the base activator was dropped. An optical image of the results of this experiment is shown in FIG. 7.

Example 6. Comparison of Spectral Evolution for Catechol and $FeCl_3$ Solutions with and without Amplifier after Addition of Activator The base activator 4-benzylpiperidine was added into catechol and $FeCl_3$ (3:1, mol:mol) solutions with and without 10 mM base amplifier BA-BPD in Scheme 2. FIG. 8 shows time-lapse UV-Vis spectra for these solutions at room temperature within 2 h after addition of different concentrations of base activator (5 min interval). In this experiment, small molecular catechol was used to examine if base amplification could influence the response of catechol-Fe complexation to dilute base triggers. Arrows in the figures indicate evolution directions of these spectra over time, and complexes contributing to each peak are specified. Shown in figures at the left, control samples (without base amplifier) reach equilibria within minutes after activation. In contrast, spectra of samples containing 10 mM BA-BPD keep evolving within 2 h, reaching similar final states.

Catechol-Fe complexation is in a dynamic equilibrium under basic conditions. Thus, the advantages of this type of self-strengthening polymer is that the gel formed after the strengthening process can still self-heal due to its ability to heal small cracks afterwards the strengthening process.

Other materials using catechol-Fe complexation that are under neutral conditions require manual addition of basic solutions to trigger the healing event. This usually requires adding a base trigger for healing to occur. In contrast, the use of encapsulated/latent base triggers would impart autonomy to the material. Since base amplifiers would be incorporated in the matrix, even dilute base triggers released due to a small damage event or stressor could elicit the self-strengthening process.

Additionally, self-healing materials that have previously utilized catechol-Fe complexation are mostly hydrogels swollen with basic solutions, causing gradual oxidation of catechol groups to o-quinone and loss of self-healing capability. Also, one notorious disadvantage of self-healing materials based on dynamic bonds is creeping over time. In this disclosure case, base triggers would be encapsulated first and only released upon damage to initiate the self-strengthening process. Therefore, a longer life-time is achieved compared to reported systems, since oxidation of catechol under neutral conditions is much slower than that under basic conditions. Also, before any self-strengthening process occurs, the disclosed composite material does not form the dynamic bonds, and therefore minimizes creeping under stress.

Example 7. Comparison of a Polymer Solution with Both Amplifier and Activator Vs. A Polymer Solution with Activator Only

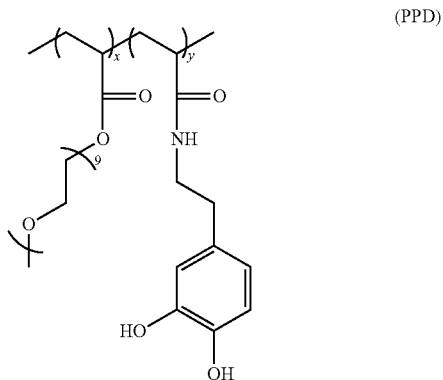

(PPD)

Figure 9:
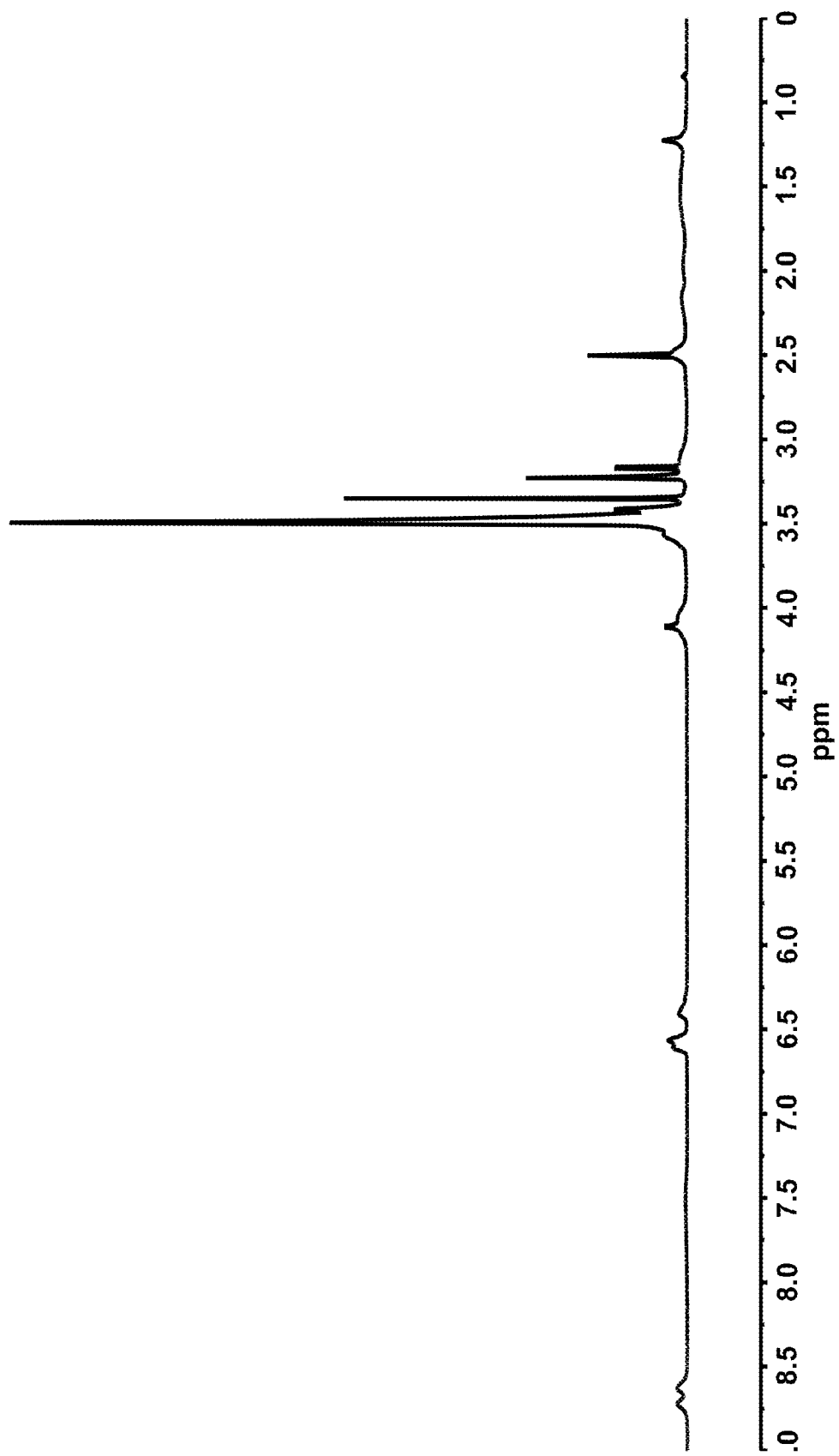
FIG. 9. $^1$H NMR of poly[poly(ethylene glycol) methyl ether acrylate-dopamine acrylamide] (PPD) in DMSO-$d_6$.
Figure 10:
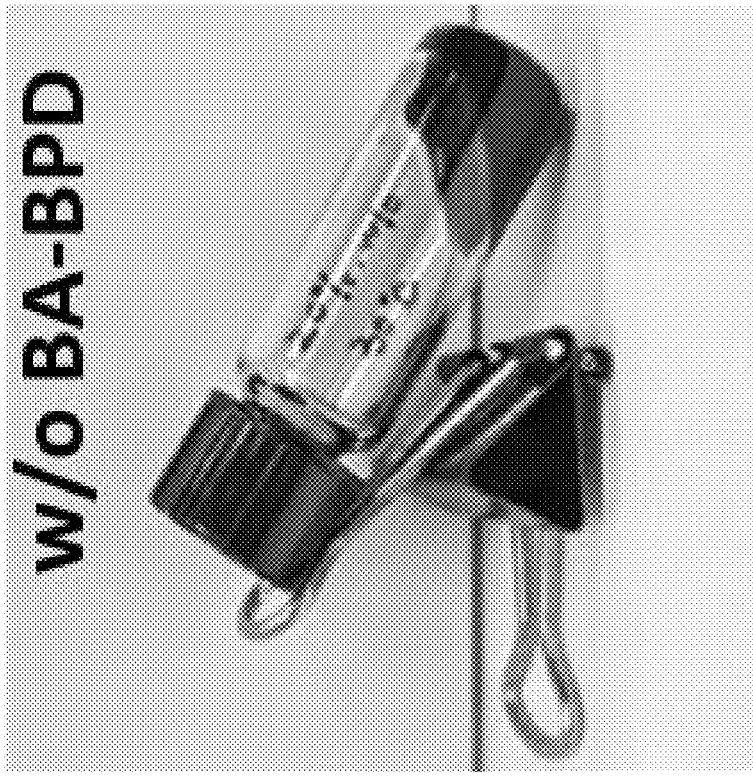
FIG. 10. Samples of PPD+FeCl$_3$ in 1 mM TFA/DMSO with and without base amplifier BA-BPD after addition of base activator.
Figure 10:
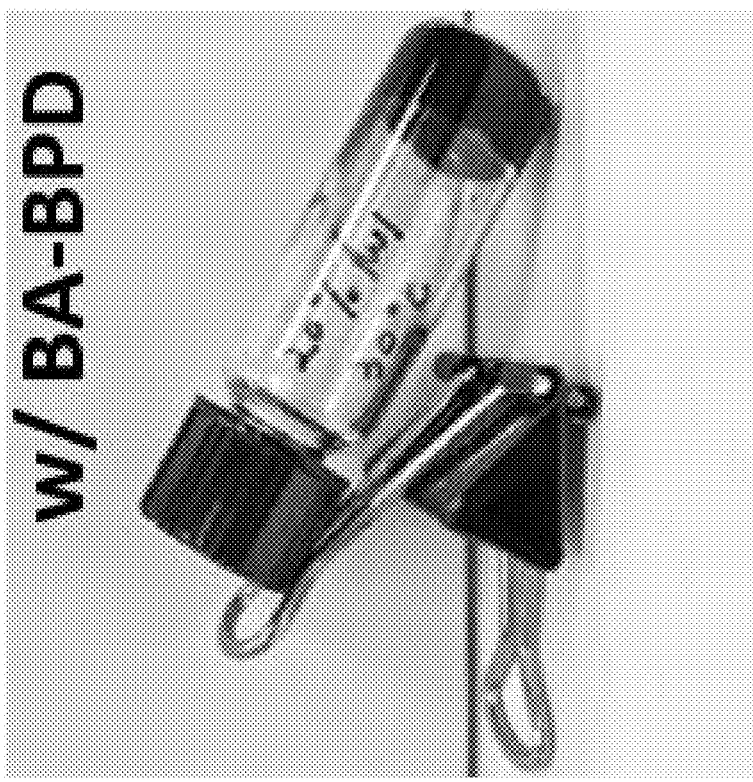

Poly[poly(ethylene glycol) methyl ether acrylate-dopamine acrylamide] (PPD) was synthesized by reversible addition-fragmentation chain transfer (RAFT) polymerization followed by a substitution reaction. Briefly, certain amounts of poly(ethylene glycol) methyl ether acrylate, pentafluorophenyl acrylate, azobisisobutyronitrile (initiator), and 2-cyano-2-propyl dodecyl trithiocarbonate (chain transfer agent) were dissolved in dioxane. $^1$H NMR of PPD in DMSO-$d_6$ are shown in FIG. 9. After purged with nitrogen for 1 h, the mixture was placed in a 65° C. oil bath, and reacted for 24 h. The polymerization solution was then quenched by exposure to air, and precipitated into diethyl ether. For the second step, a DMF solution of the polymer, dopamine hydrochloride, and trimethylamine was degassed for 30 min and reacted at 50° C. After 24 h, the mixture was precipitated into diethyl ether, before dialysis against DI water. The final polymer PDD was obtained by freeze-drying. 20% (w/v) poly[poly(ethylene glycol) methyl ether acrylate-dopamine acrylamide] (PPD)+FeCl$_3$ (catechol: Fe=3:1, mol:mol) solutions were prepared in 1 mM TFA/DMSO with and without base amplifier BA-BPD. After addition of the base activator 4-benzylpiperidine (amplifier: activator=20:1, mol:mol), both solutions were heated to 30° C. Optical images of the results of this experiment are shown in FIG. 10: 3.5 h after activation, only the sample containing BA-BPD undergoes sol-gel transition, yielding a purple gel, while the sample free of BA-BPD remains a green solution. Scheme 3 shows such sol-gel transition. Since the activator added into the solution is below the threshold to induce significant cross-linking, the control sample without base amplifier remains a solution. Only when base amplifier is present can base continue to accumulate upon activation and leading to the formation of a gel.

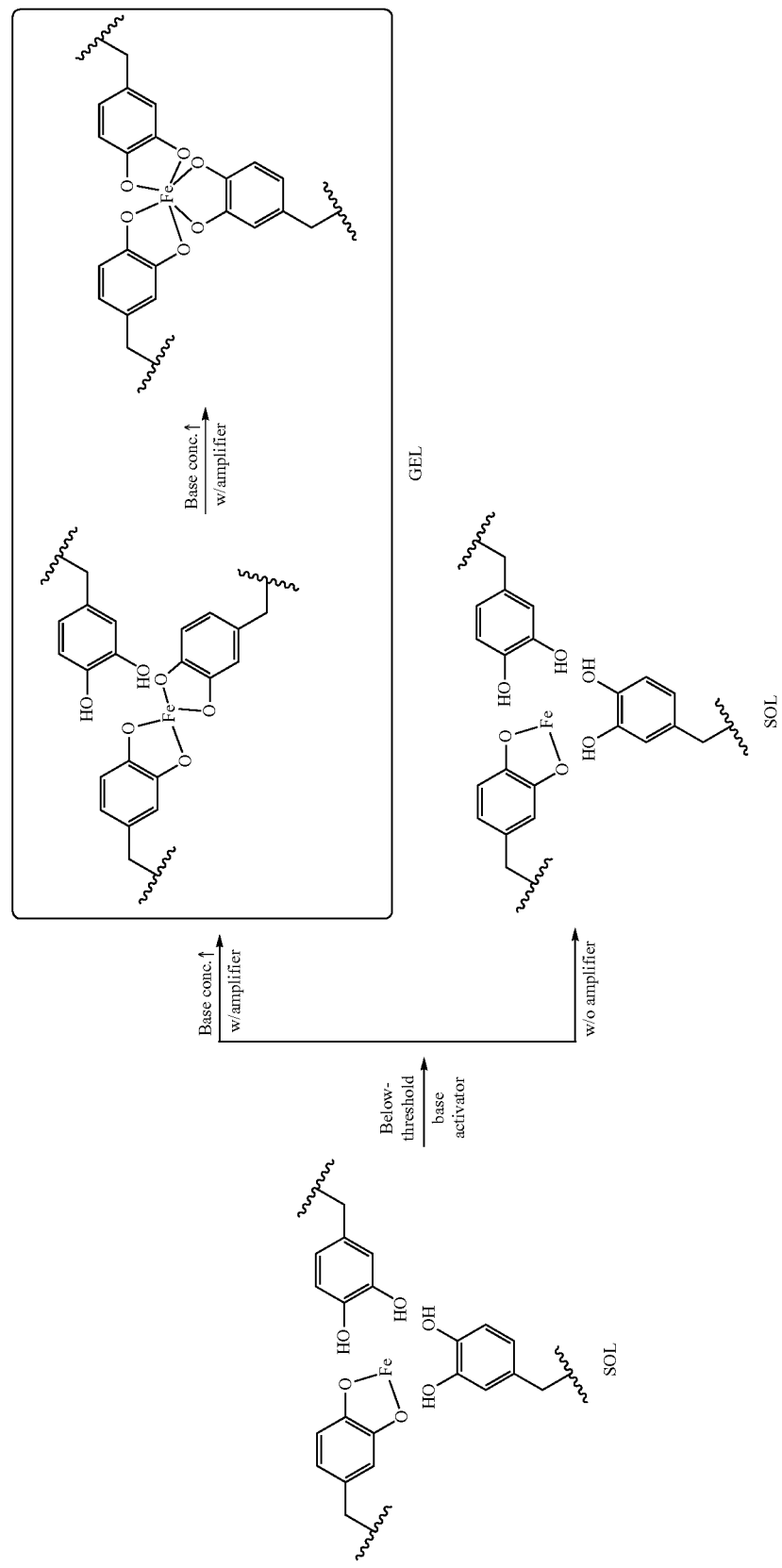
Scheme 3. A catechol-containing polymer undergoing a sol-gel transition when base amplifier is present.

Example 8. Modulus Change of Polymer Solutions Containing Amplifier and Activator

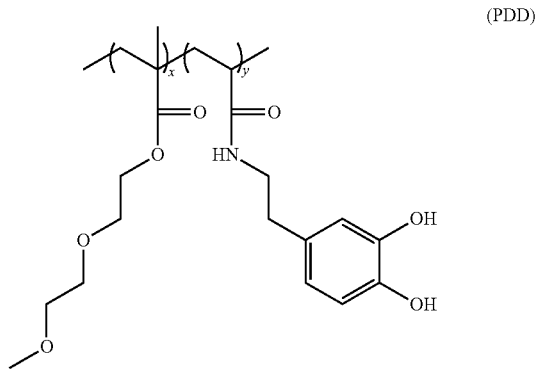

(PDD)

Figure 11:
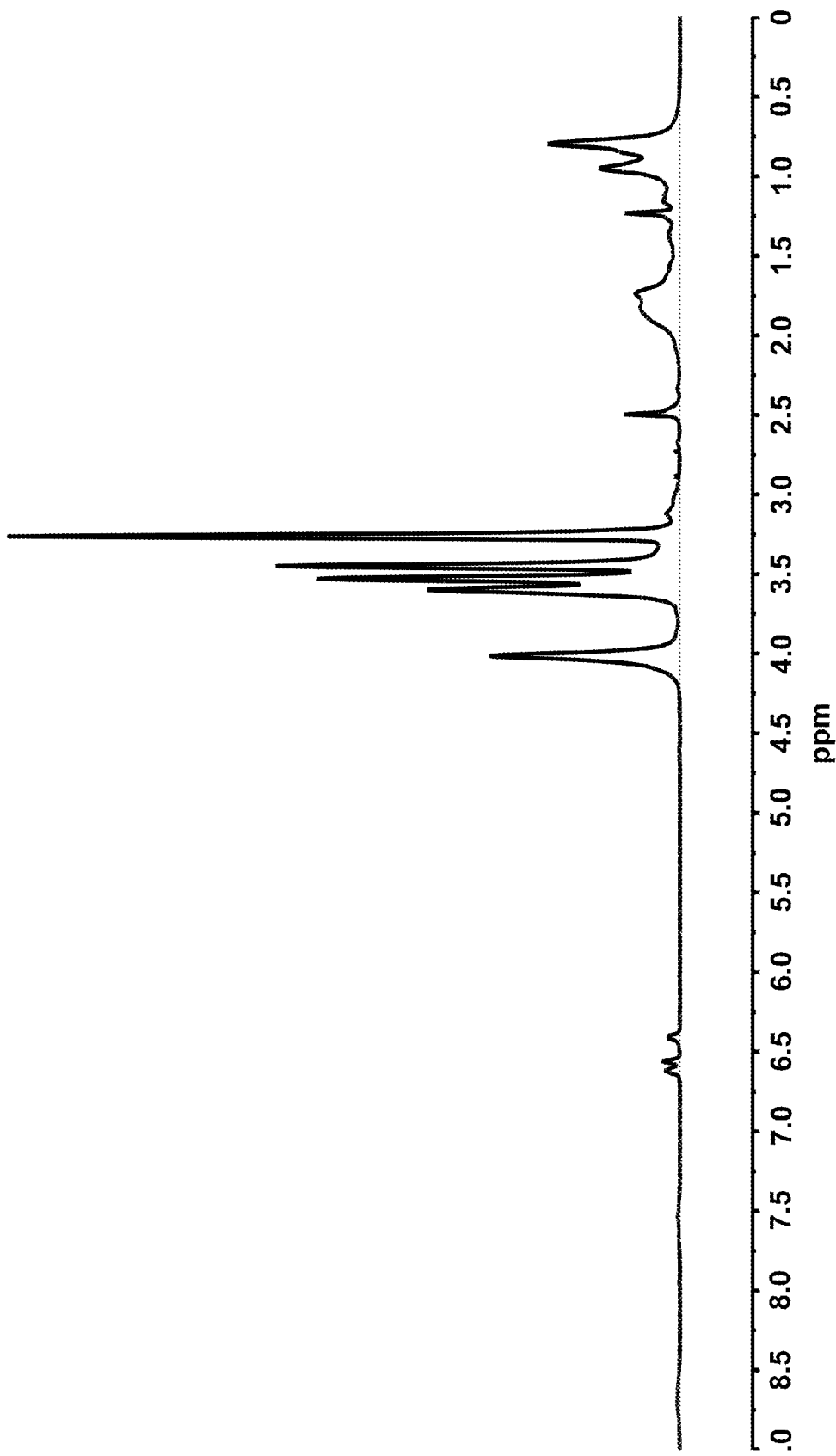
FIG. 11. $^1$H NMR of poly[di(ethylene glycol) methyl ether methacrylate-dopamine acrylamide] (PDD) in DMSO-$d_6$.
Figure 12A:
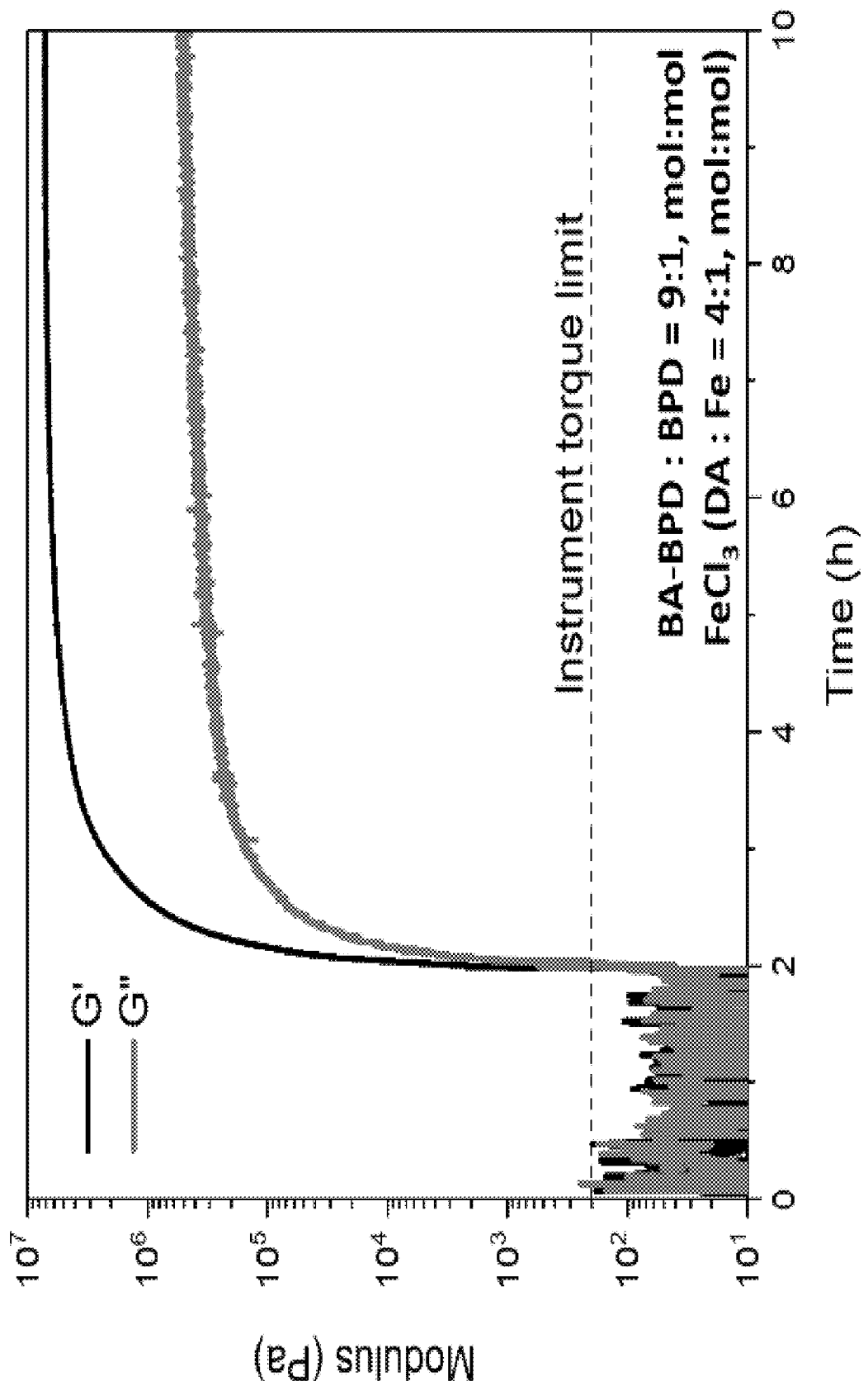
FIG. 12A-12C. Rheological properties showing base amplifier BA-BPD enables sharp sol-gel transition in the presence of below-threshold activator, and at least 4 orders of magnitude increase of sample moduli.
Figure 12B:
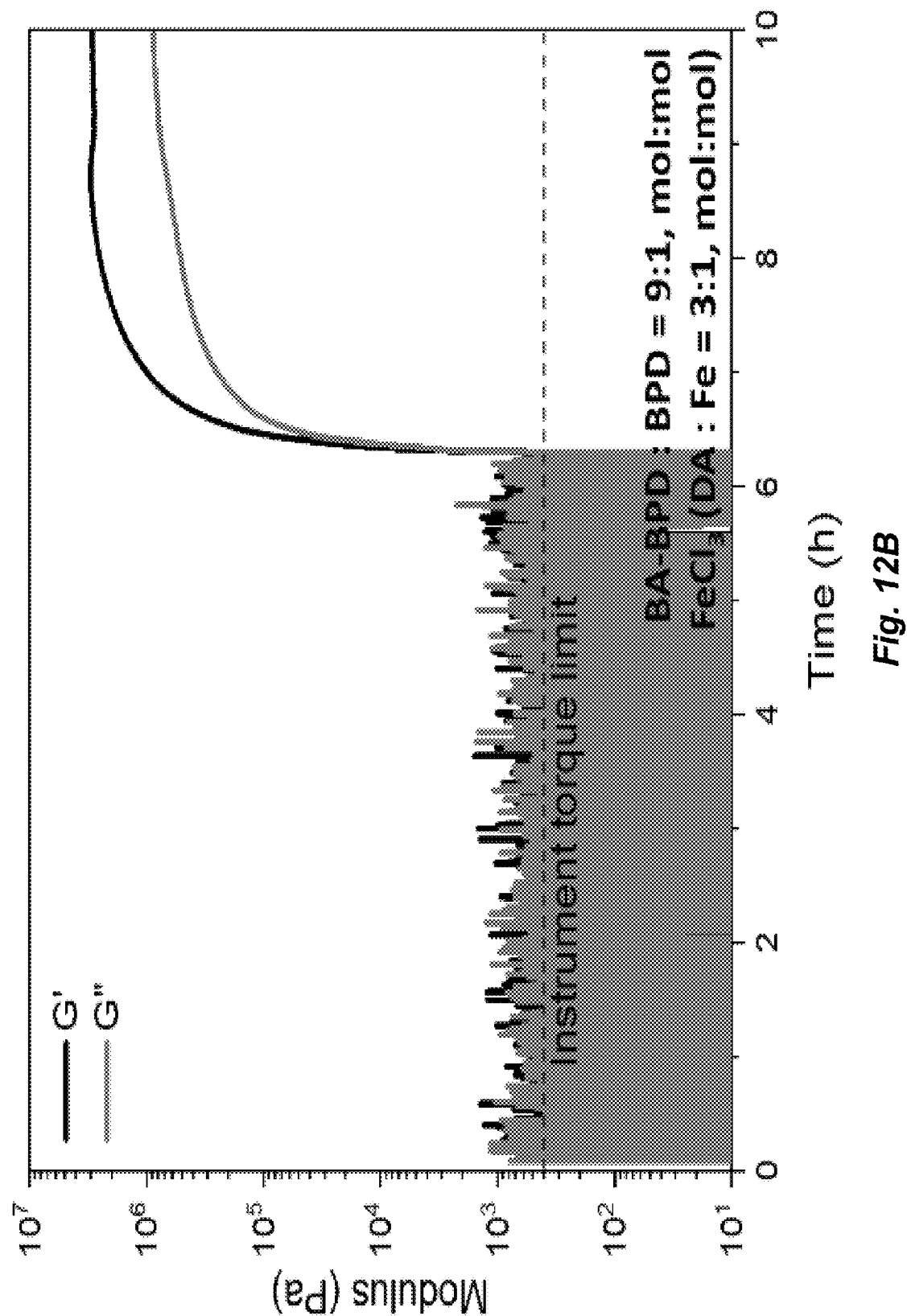
Figure 12C:
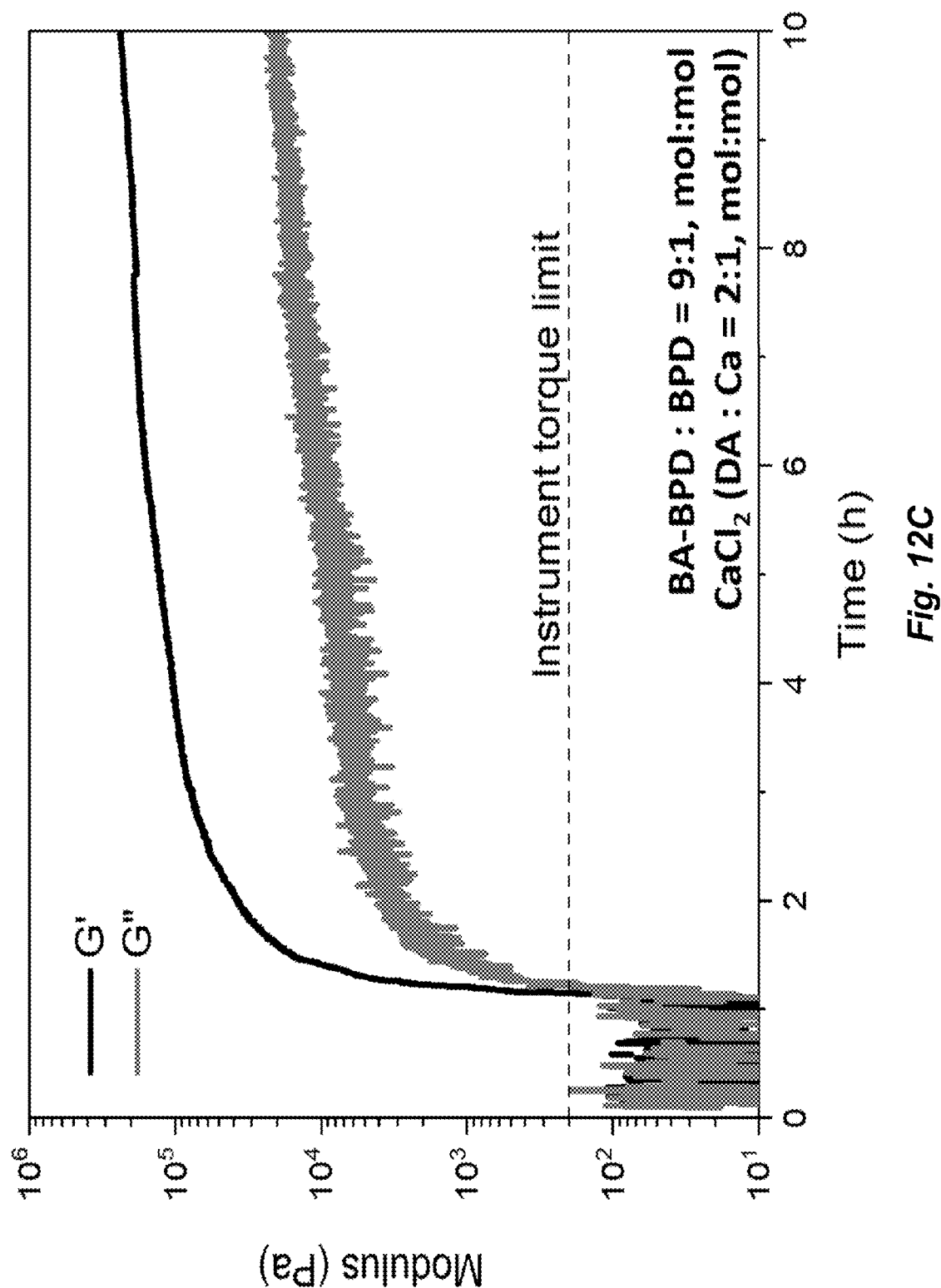
Figure 13A:
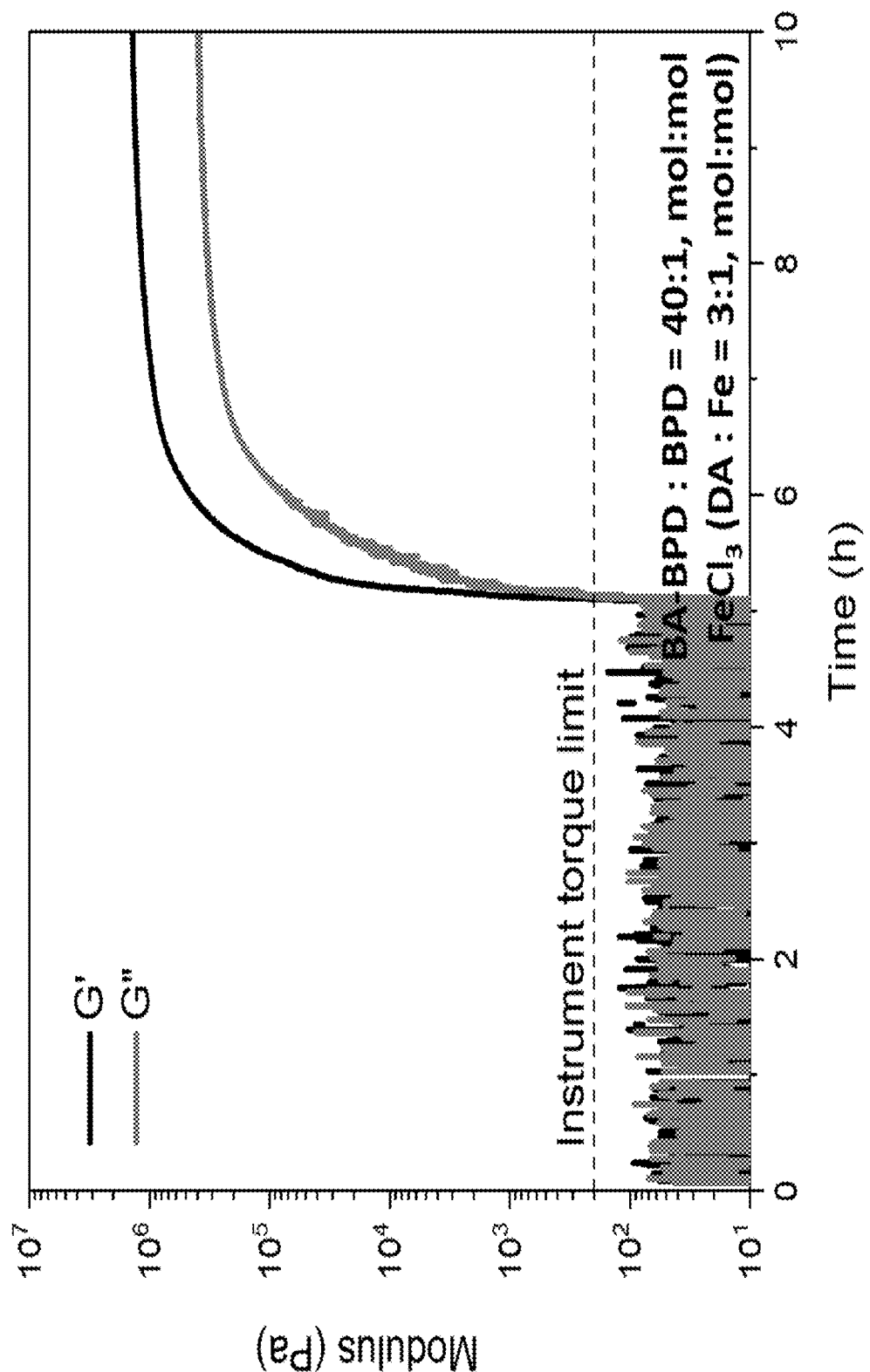
FIG. 13A-13B. Rheological properties from 20% (w/v) PDD solution containing BA-BPD and FeCl$_3$.
Figure 13B:
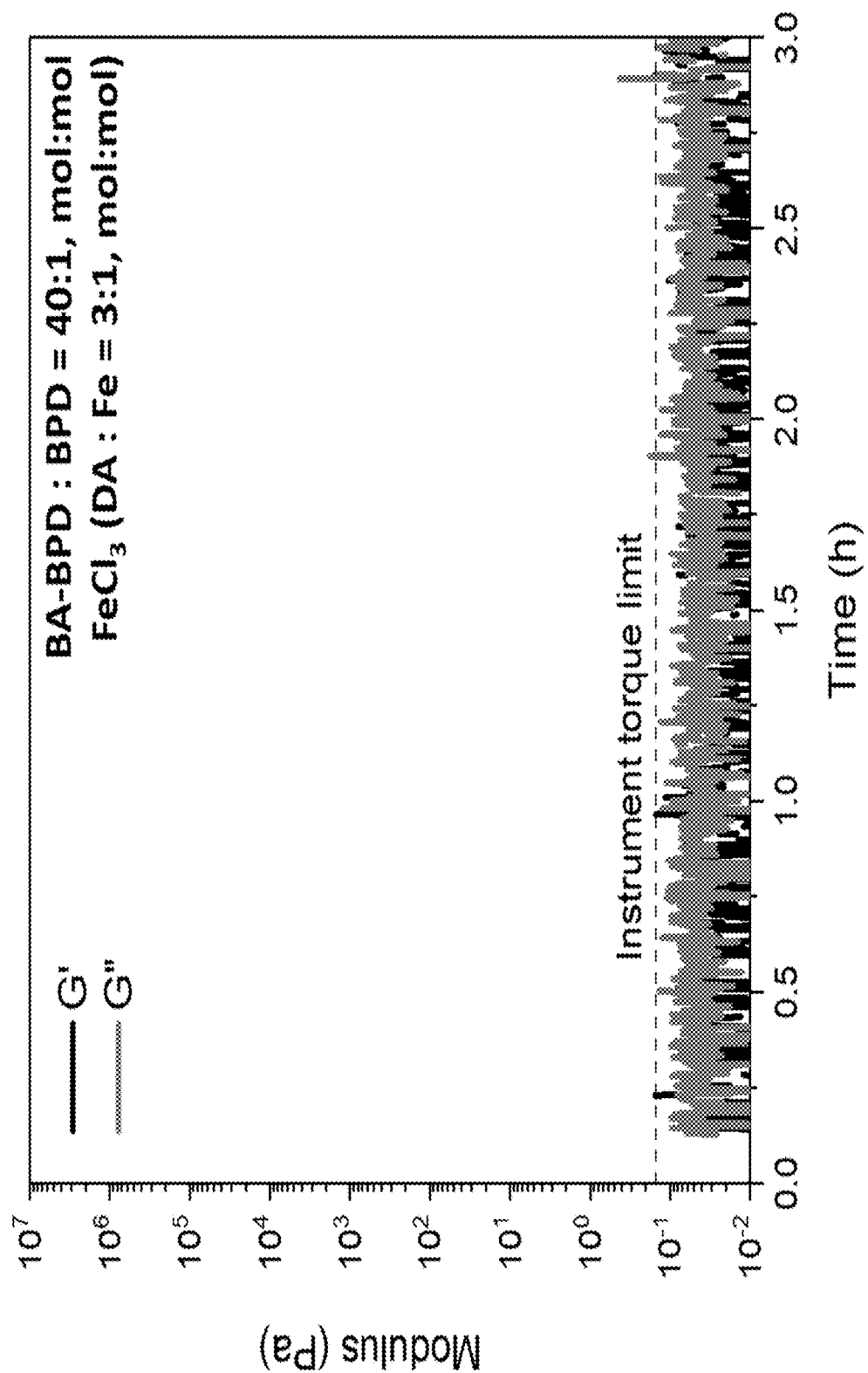

Poly[di(ethylene glycol) methyl ether methacrylate-dopamine acrylamide] (PDD) was synthesized by the same method as PPD, except i) 4-cyano-4-(dodecylsulfanylthiocarbonyl)sulfanyl pentanoic acid was used as the chain transfer agent; ii) DMF was used as the solvent; and iii) polymerization was conducted at 70° C. $^1$H NMR of PPD in DMSO-$d_6$ is shown in FIG. 11. 30% (w/v) Poly[di(ethylene glycol) methyl ether methacrylate-dopamine acrylamide] (PDD) and BA-BPD (Scheme 2) solutions were prepared in 1 mM TFA/DMSO containing different metal salts. The mechanism of sol-gel transition is the same as shown in Scheme 3. It is noted that in rheology tests the ratio of amplifier to activator is kept reasonably high so that measurement could be finished within a reasonable time, and that amplifier concentration is kept relatively low so as to avoid sample overflow and experimental errors. After addition of a certain amount of base activator 4-benzylpiperidine (amplifier:activator=9:1, mol:mol), samples were loaded onto a rheometer set at 35° C. FIG. 12 shows that existence of base amplifier BA-BPD enables sharp sol-gel transition in the presence of below-threshold activator, and at least 4 orders of magnitude increase of sample moduli. It should be noted that moduli of initial solution samples in FIG. 12 are below the instrument torque limit and results in background noise. Consistent with vial tests, neither gelation nor modulus increase was observed for control samples without base amplifier (data not shown). FIG. 13A shows another rheology test on 20% (w/v) PDD solution containing BA-BPD and FeCl$_3$ (DA:Fe=3:1, mol:mol), suggesting that even when the ratio of activator to amplifier is reduced down to 1:40, the system can still respond productively and form a gel at the end. FIG. 13B resolves the moduli during the first 3 h after activation, and confirms a modulus increase of over 7 orders of magnitude before and after gelation.

SUMMARY OF DISCLOSURE

Extrinsic self-healing is a straightforward approach to healing materials damages and elongating material lifetime, but usually requires long healing time and high healing temperature due to limited loading of healing agents and slow delivery of healing agents to the damage sites. In this disclosure, improvements in low-temperature extrinsic self-strengthening via incorporation of acid or base amplifiers is described. Specifically, the improvement is achieved by solving the problems faced by conventional extrinsic self-healing materials.

The disclosure features the low requirement of energy input, indicated by small amounts of triggers and relatively low temperature for this composition and methods to work. Also, the versatile usage of acids and bases in chemical reactions imparts high freedom of derivatizing in this disclosure without any change of the key components, i.e., acid or base amplifiers. In combination with extrinsic self-strengthening, a high strengthening rate is expected to be achieved at relatively low temperatures (e.g., room temperature or near room temperature).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A self-reinforcing material comprising:
   (a) a polymer doped with a metal salt, and a chemical amplifier, wherein the chemical amplifier is capable of amplifying a change in pH at a locus within the polymer, and
   (b) a plurality of triggerable reservoirs comprising an activator, wherein the triggerable reservoir is capable of releasing a catalytic quantity of the activator that induces the autocatalytic decomposition of the chemical amplifier in response to a mechanical stimulus at the locus;
   wherein the locus is any position within the polymer where the triggerable reservoir is located;
   wherein the chemical amplifier amplifies a change in local pH at the locus when the chemical amplifiers react with the catalytic quantity of the activator released by the triggerable reservoir in response to the mechanical stimulus, thereby changing the chemical and physical properties of the polymer.

2. The self-reinforcing material of claim 1 wherein the metal salt is a salt of iron, nickel, copper, zinc, magnesium, chromium, cobalt, tin, aluminum, calcium, or a combination thereof.

3. The self-reinforcing material of claim 1 wherein the polymer comprises a polysiloxane, a poly[poly(ethylene glycol) acrylate], a polybutadiene, an epoxy, a catechol-containing polymer, or a combination thereof.

4. The self-reinforcing material of claim 3 wherein the polymer comprises polydimethylsiloxane, poly[poly(ethylene glycol) methyl ether acrylate-dopamine acrylamide] (PPD), poly[di(ethylene glycol) methyl ether methacrylate-dopamine acrylamide] (PDD), vinyl-polybutadiene, cis-polybutadiene, a phenolic epoxy, or a combination thereof.

5. The self-reinforcing material of claim 3 wherein the triggerable reservoir is a microcapsule, a core-shell fiber, a mechanophore, or a combination thereof.

6. The self-reinforcing material of claim 5 wherein the triggerable reservoir comprises the activator, wherein the activator is an acid catalyst or a base catalyst.

7. The self-reinforcing material of claim 6 wherein the chemical amplifier is an acid amplifier or a base amplifier.

8. The self-reinforcing material of claim 7 wherein the ratio of the acid or base amplifier to the acid or base catalyst ranges from about 5:1 to about 500:1, and wherein the acid catalyst is trifluoroacetic acid or the base catalyst is 4-benzylpiperidine.

9. The self-reinforcing material of claim 7 wherein the base amplifier is:

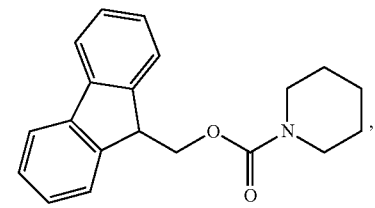
(BA-PD)

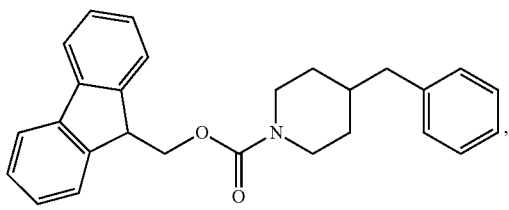
(BA-BPD)

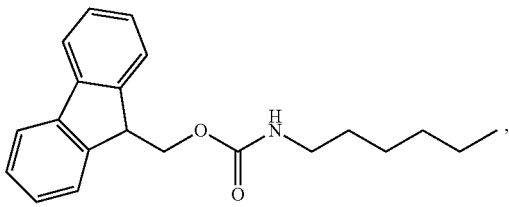
(BA-HA)

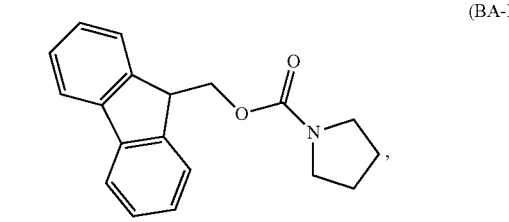
(BA-PRL)

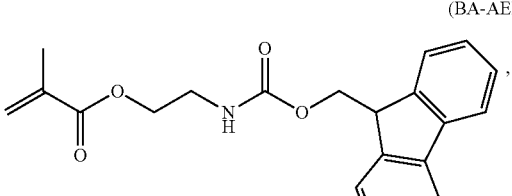
(BA-AEMA)

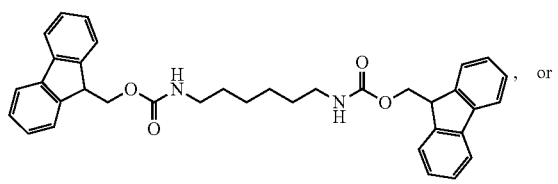
(BA-HMDA), or

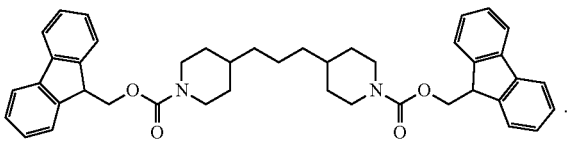
(BA-TMDPD).

10. The self-reinforcing material of claim 7 wherein the acid amplifier is:

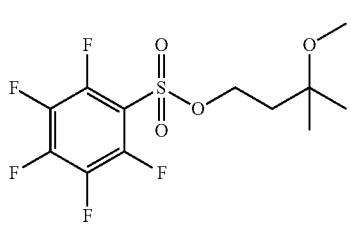
(AA-1)

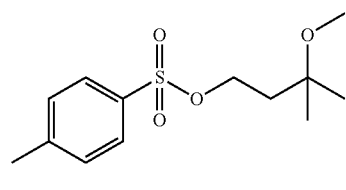
(AA-2)

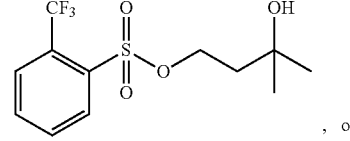
(AA-3), or

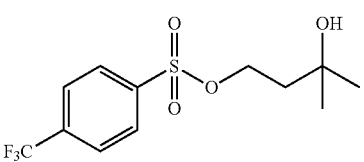
(AA-4).

11. The self-reinforcing material of claim 7, wherein the base amplifier decomposes upon contact with the base catalyst to autocatalytically release a second base.

12. The self-reinforcing material of claim 7, wherein the acid amplifier decomposes upon contact with the acid catalyst to autocatalytically release a second acid.

13. The self-reinforcing material of claim 7 wherein the polymer is cross-linked at the locus after the activator is released.

14. The self-reinforcing material of claim 13 wherein the cross-linked polymer comprises a cross-linked metallopolymer.

15. The self-reinforcing material of claim 7 wherein the acid amplifier is stabilized by a base.

16. The self-reinforcing material of claim 7 wherein the base amplifier is stabilized by an acid.

17. The self-reinforcing material of claim 16 wherein the base amplifier is stabilized by trifluoroacetic acid.

18. A method to prepare a self-reinforcing material, the method comprising:
coating a substrate with a polymer layer doped with a stabilized acid or base amplifier, metal salts, and a plurality of triggerable reservoirs comprising an acid or base catalyst, wherein the acid or base amplifier is capable of amplifying a change in pH at a locus within the polymer layer, and wherein the triggerable reservoir is capable of releasing a catalytic quantity of the acid catalyst or the base catalyst that induces the autocatalytic decomposition of the acid or base amplifier in response to a mechanical stimulus at the locus, wherein the locus is any position within the polymer where the triggerable reservoir is located;

wherein when a mechanical stimulus causes damage to the coated substrate, the acid or base amplifier amplifies a change in local pH at the locus when it reacts with the catalytic quantity of the acid catalyst or the base catalyst released by the triggerable reservoir in response to the mechanical stimulus, thereby forming a cross-linked metallopolymer to form a self-reinforced material at the locus.

19. The method of claim 18 wherein the metallopolymer is formed at a temperature of about 15° C. to about 35° C.

20. The method of claim 18 wherein the metallopolymer is formed by heating the locus to a temperature up to about 100° C.

* * * * *